(12) United States Patent
O'Hara et al.

(10) Patent No.: US 10,493,093 B2
(45) Date of Patent: *Dec. 3, 2019

(54) COMPOSITION AND METHODS OF SCREENING

(71) Applicant: OPTIBIOTIX LIMITED, Heslington, York (GB)

(72) Inventors: Stephen Patrick O'Hara, Heslington (GB); Robert Rastall, Reading (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/901,637

(22) Filed: Feb. 21, 2018

(65) Prior Publication Data

US 2018/0177817 A1 Jun. 28, 2018

Related U.S. Application Data

(63) Continuation of application No. 15/034,420, filed as application No. PCT/GB2014/053303 on Nov. 5, 2014, now Pat. No. 9,913,857.

(30) Foreign Application Priority Data

Nov. 5, 2013 (GB) .................................. 1319539.1

(51) Int. Cl.
| | | |
|---|---|---|
| *A61K 9/00* | (2006.01) | |
| *A61K 9/50* | (2006.01) | |
| *C12Q 1/02* | (2006.01) | |
| *A61K 49/00* | (2006.01) | |
| *A61K 35/74* | (2015.01) | |
| *A61K 31/715* | (2006.01) | |
| *A61K 35/741* | (2015.01) | |
| *A61K 45/06* | (2006.01) | |
| *A23L 29/269* | (2016.01) | |
| *A23L 33/135* | (2016.01) | |
| *A23L 33/26* | (2016.01) | |

(52) U.S. Cl.
CPC .......... *A61K 31/715* (2013.01); *A23L 29/269* (2016.08); *A23L 33/135* (2016.08); *A23L 33/26* (2016.08); *A61K 9/0053* (2013.01); *A61K 9/50* (2013.01); *A61K 35/741* (2013.01); *A61K 45/06* (2013.01); *A61K 49/0004* (2013.01); *C12Q 1/025* (2013.01); *A23V 2002/00* (2013.01); *A23Y 2220/00* (2013.01); *A23Y 2220/35* (2013.01); *A23Y 2220/71* (2013.01); *G01N 2333/335* (2013.01); *G01N 2333/938* (2013.01); *G01N 2500/10* (2013.01)

(58) Field of Classification Search
CPC ........ A61K 31/715; A61K 45/06; A61K 9/50; A61K 35/741; A61K 49/0004; A61K 2300/00; A23L 29/269; G01N 2333/335; C12Q 1/025; A23V 2200/328
See application file for complete search history.

(56) References Cited

U.S. PATENT DOCUMENTS

| | | | |
|---|---|---|---|
| 9,913,857 B2 * | 3/2018 | O'Hara | A23L 33/135 |
| 2008/0254011 A1 | 10/2008 | Rothschild et al. | |
| 2009/0214594 A1 | 8/2009 | Fichot et al. | |
| 2011/0117629 A1 | 5/2011 | Lin et al. | |
| 2011/0177044 A1 | 7/2011 | Thomas et al. | |
| 2011/0206649 A1 | 8/2011 | Bergonzelli Degonda et al. | |
| 2012/0263696 A1 | 10/2012 | Roos | |

FOREIGN PATENT DOCUMENTS

| | | |
|---|---|---|
| EP | 0 856 259 A1 | 8/1998 |
| EP | 2 216 036 A1 | 8/2010 |
| WO | 2004/074496 A1 | 9/2004 |
| WO | 2010/124387 A1 | 11/2010 |

OTHER PUBLICATIONS

Tzortzis, G. et al. "In vitro evaluation of the fermentation properties of galactooligosaccharides synthesized by [alpha]-galactosidase from Lactobacillus Reuteri", Applied Microbiology and Biotechnology, Springer, DE, vol. 64, No. 1, Jan. 1, 2004 (Jan. 1, 2004), pp. 106-111, XP002285616, ISSN: 0175-7598, DOI: 10.1007/S00253-003-1427-Z.

Park, Yoo Heon et al. "Effect of Dietary Inclusion of Lactobacillus acidophilus ATCC 43121 on Cholesterol Metabolism in Rats", Journal of Microbiology and Biotechnology, vol. 17, No. 4, Apr. 1, 2007 (Apr. 1, 2007), pp. 655-662, XP002734586, Seoul , Korea ISSN: 1017-7825.

Noh, D. O. et al. "Incorporation of Cholesterol into the Cellular Membrane of Lactobacillus acidophilus ATCC 43121", Journal of Dairy Science, American Dairy Science Association, US, vol. 80, No. 12, Dec. 1, 1997 (Dec. 1, 1997), pp. 3107-3113, XP027048111, ISSN: 0022-0302.

International Search Report and Written Opinion issued in corresponding International Application No. PCT/GB2014/053303 dated Feb. 4, 2015.

International Search Report and Written Opinion issued in corresponding International Application No. PCT/GB2014/053290 dated Feb. 4, 2015.

International Search Report and Written Opinion issued in corresponding International Application No. PCT/GB2014/053301 dated Feb. 4, 2015.

International Search Report and Written Opinion issued in corresponding International Application No. PCT/GB2014/053302 dated Feb. 4, 2015.

(Continued)

*Primary Examiner* — Padmavathi Baskar
(74) *Attorney, Agent, or Firm* — Christopher S. Dodson; Nexsen Pruet, PLLC

(57) ABSTRACT

The present invention relates to a prebiotic composition comprising a microbially produced oligosaccharide, wherein the oligosaccharide is characterized by being selective for a pre-determined probiotic bacterial strain and also capable of being produced by the pre-determined probiotic bacteria by reverse enzyme action. The present invention also relates to methods of screening a composition suitable for use as a prebiotic and methods for screening of prebiotics for incorporation into synbiotic formulations.

13 Claims, 19 Drawing Sheets

(56) References Cited

OTHER PUBLICATIONS

Al-Fataftah, A. et al., "Enrichment of vitamin B12 and B6 and lowering cholesterol levels of eggs by lactic acid bacteria", International Journal of Food, Agriculture & Environment, vol. 11, No. 2, Jan. 1, 2013, pp. 674-678, XP55158928, Helsinki, ISSN: 1459-0255.

Al-Fataftah, A. et al., "Administration of lactic acid bacteria to enhance synthesis of vitamin B12 and B6 and lower cholesterol levels in poultry meat", International Journal of Food, Agriculture & Environment, vol. 11, No. 2, Jan. 1, 2013, pp. 604-609, XP55158929, Helsinki, ISSN: 1459-0255.

Kumar R., et al., "Bile Salt Hydrolase (Bsh) Activity Screening of Lactobacilli: In Vitro Selection of Indigenous Lactobacillus Strains with Potential Bile Salt Hydrolysing and Cholesterol-Lowering Ability", Probiotics and Antimicrobial Proteins, vol. 4, No. 3, Sep. 1, 2012, pp. 162-172, XP002734609.

Liong, M.T. et al., "Bile salt deconjugation ability, bile salt hydrolase activity and cholesterol co-precipitation ability of lactobacilli strains", International Dairy Journal, Elsevier Applied Science, Barking, GB, vol. 15, No. 4, Apr. 1, 2005, pp. 391-398, XP004715114, ISSN: 0958-6946.

Pereira, D.I.A., et al., "An In Vitro Study of the Probiotic Potential of a Bile-Salt-Hydrolyzing Lactobacillus fermentum Strain, and Determination of Its Cholesterol-Lowering Properties", Applied and Environmental Microbiology, vol. 69, No. 3, Aug. 1, 2003, pp. 4743-4752, XP055163574, ISSN: 0099-2240.

Rabiu, B.A., et al., "Synthesis and fermentation properties of novel galacto-oligosaccharides by beta-galactosidases from *Bifidobacterium* species", Applied and Environmental Microbiology, American Society for Microbiology, US, vol. 37, No. 6, Jun. 1, 2001, pp. 2526-2530, XP002613005, ISSN: 0099-2240.

Splechtna, B., et al., "Production of Prebiotic Galacto-Oligosaccharides from Lactose Using [beta]-Galactosidases from Lactobacillus reuteri", Journal of Agricultural and Food Chemistry, vol. 54, No. 14, Jul. 1, 2006, pp. 4999-5006, XP055161581, ISSN: 0021-8561.

\* cited by examiner

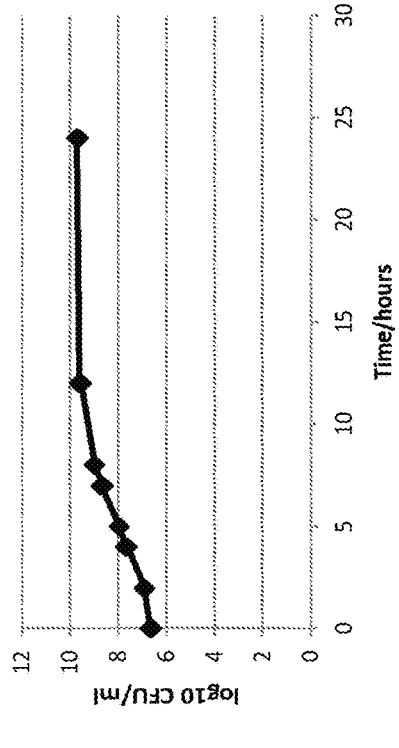
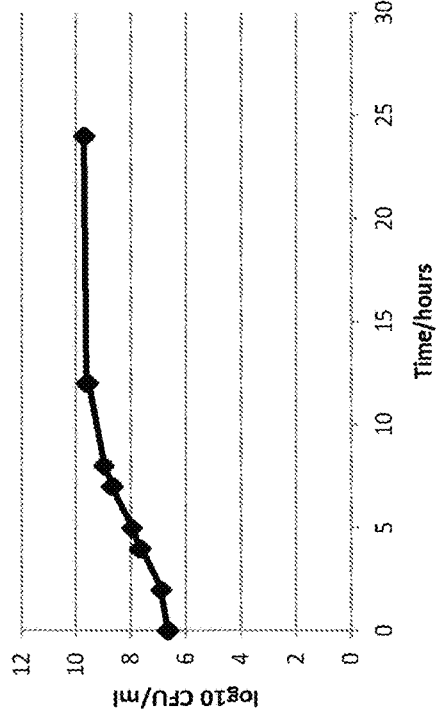
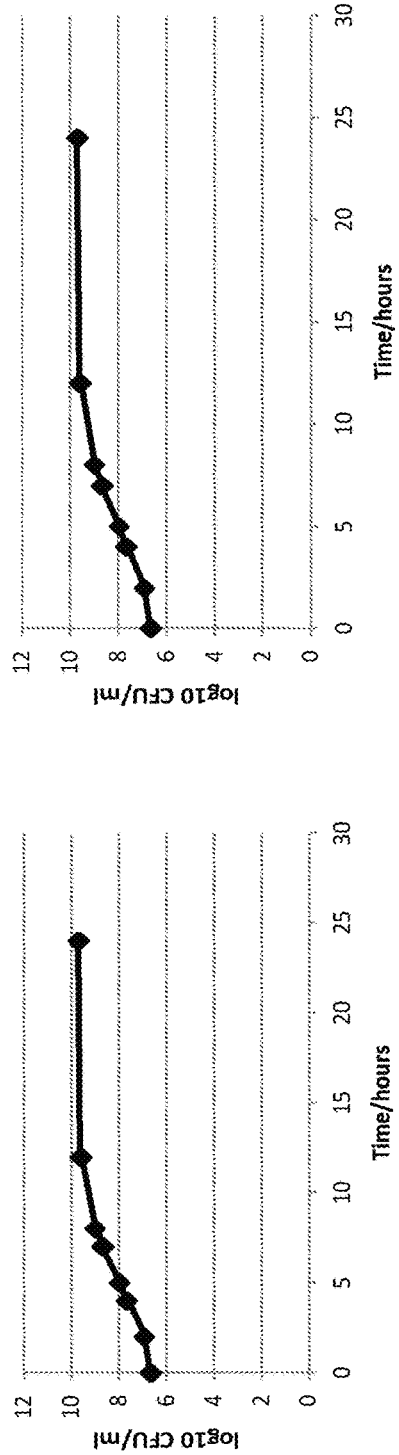
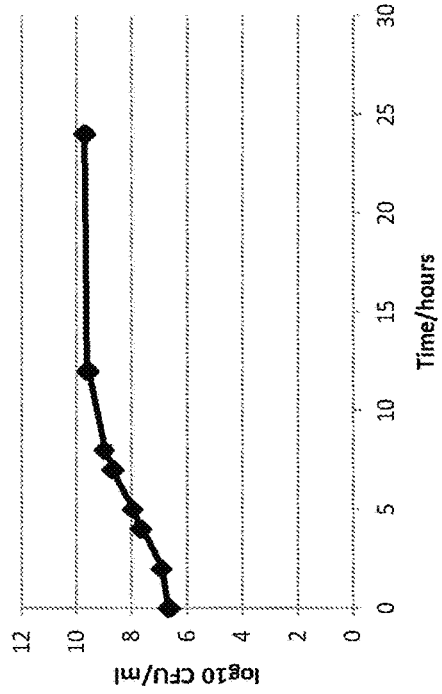
Figure 1A L. plantarum
Figure 1B L. casei
Figure 1C L. salivarius
Figure 1D L. fermentum

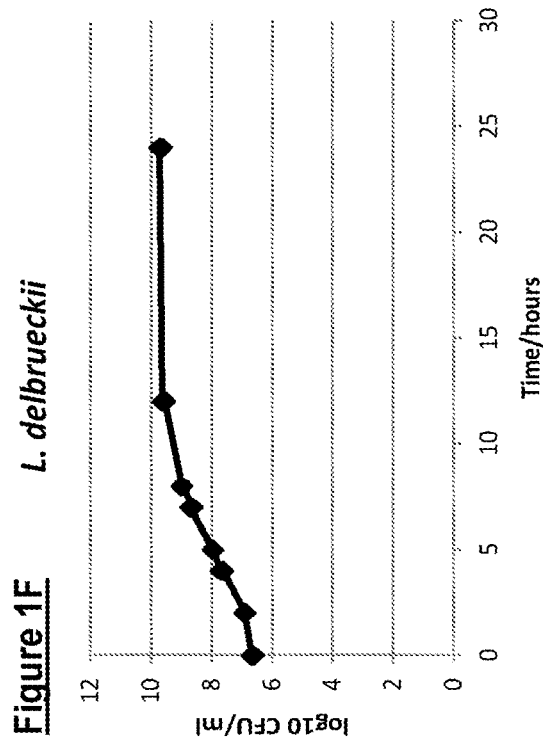
Figure 1F    L. delbrueckii
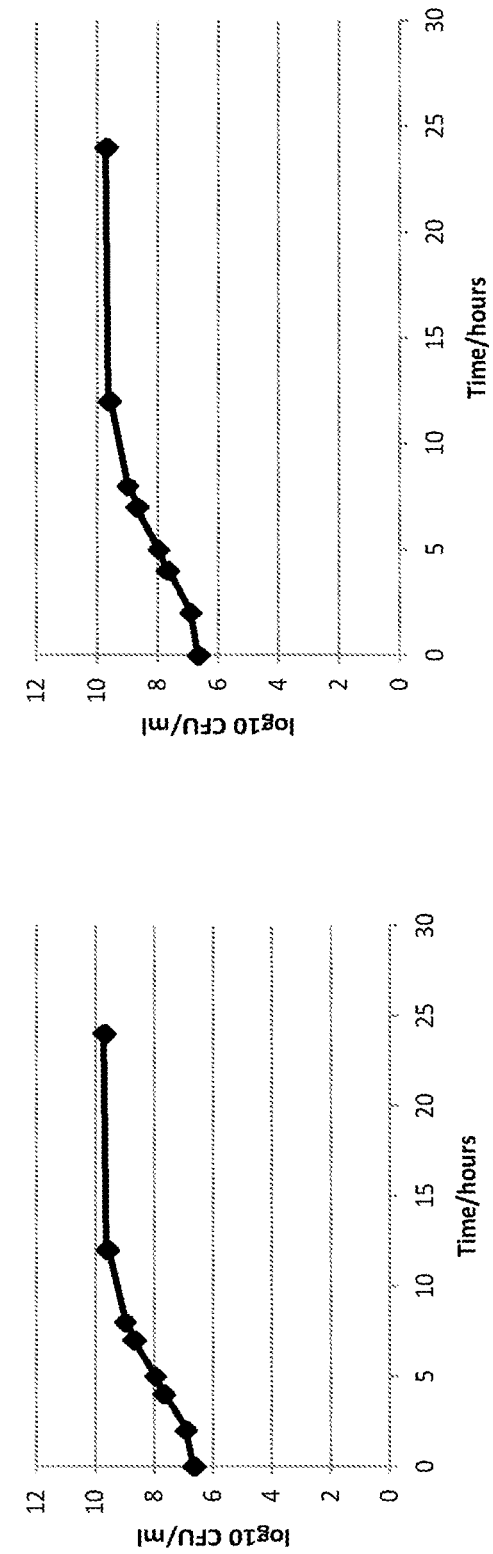
Figure 1E    L. rhamnosus

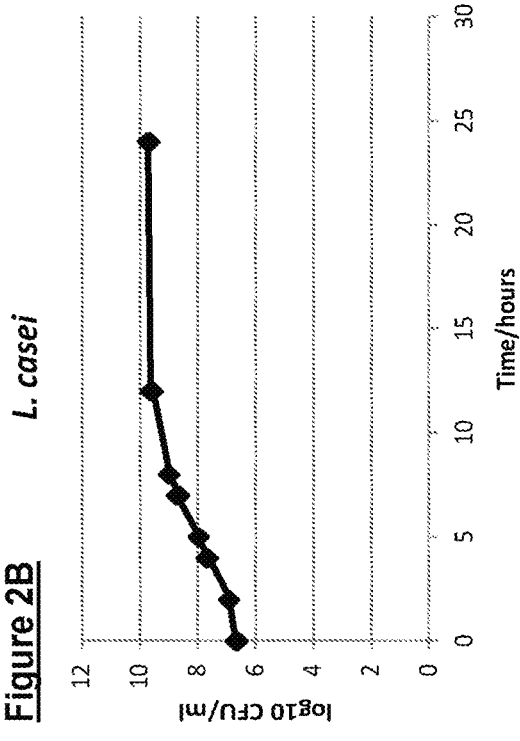
Figure 2A  L. plantarum
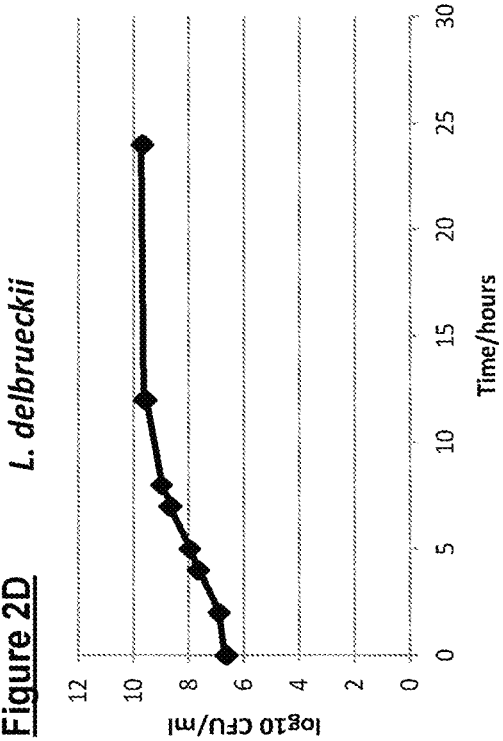
Figure 2B  L. casei
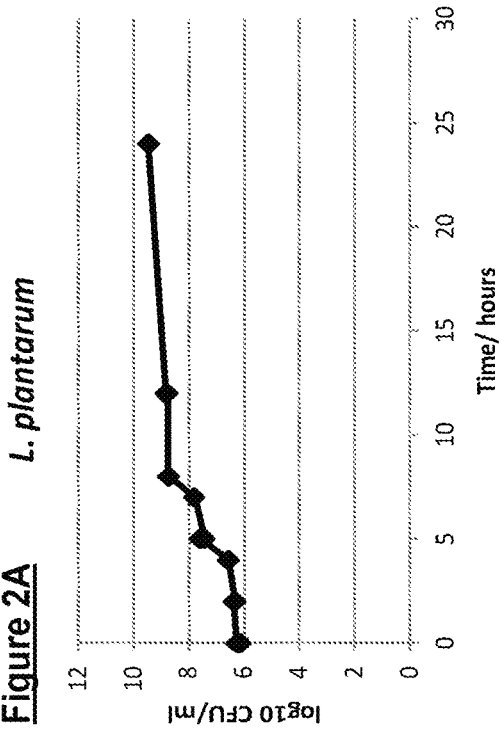
Figure 2C  L. salivarius
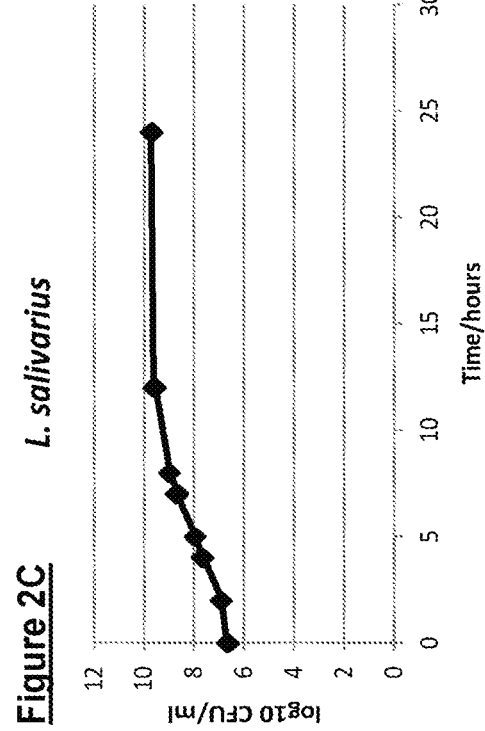
Figure 2D  L. delbrueckii

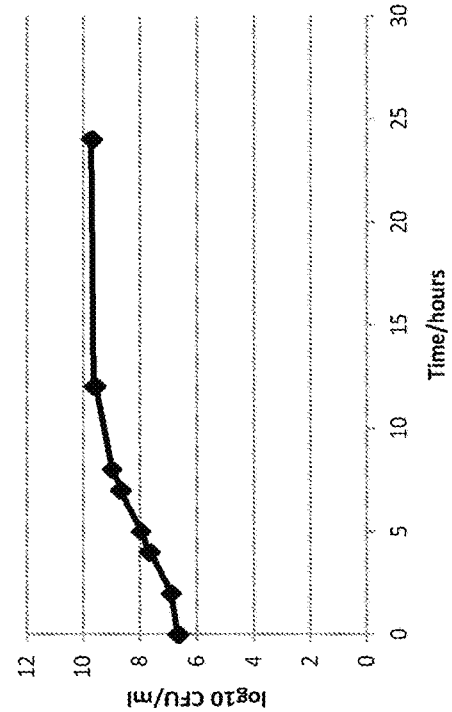
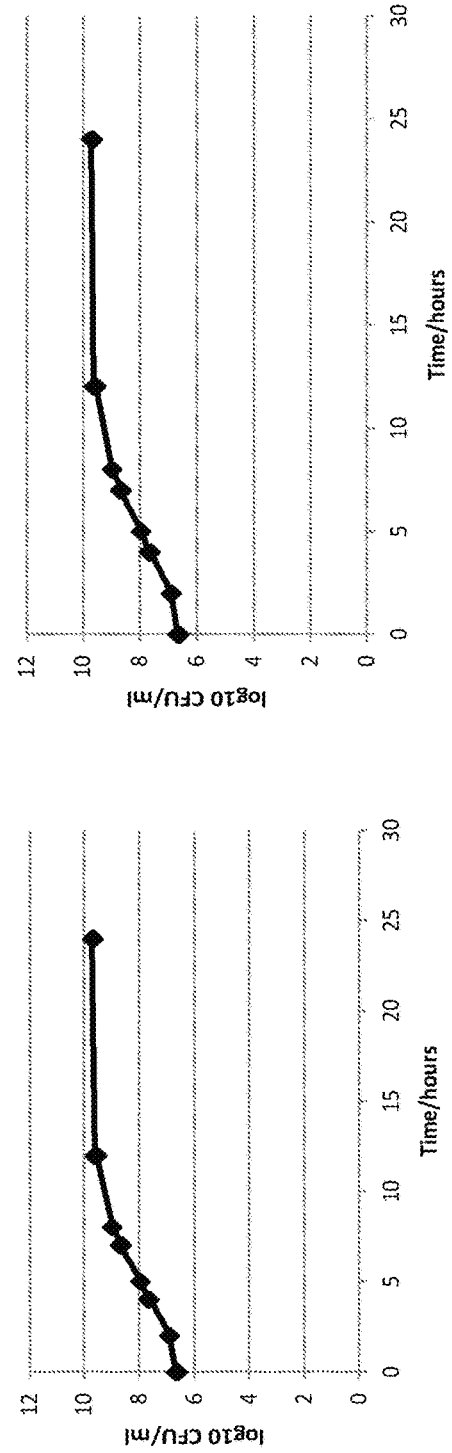
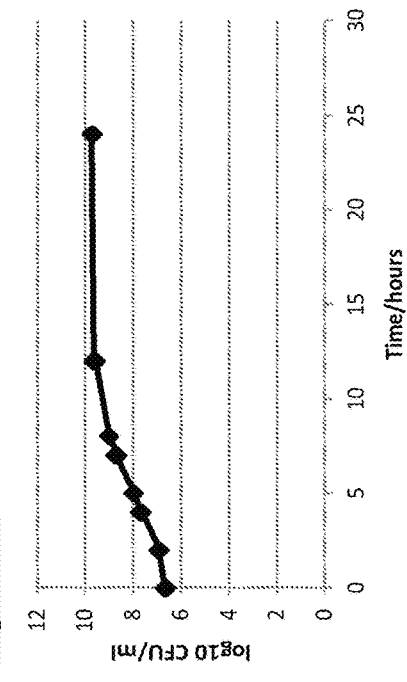

Figure 9
Sugars
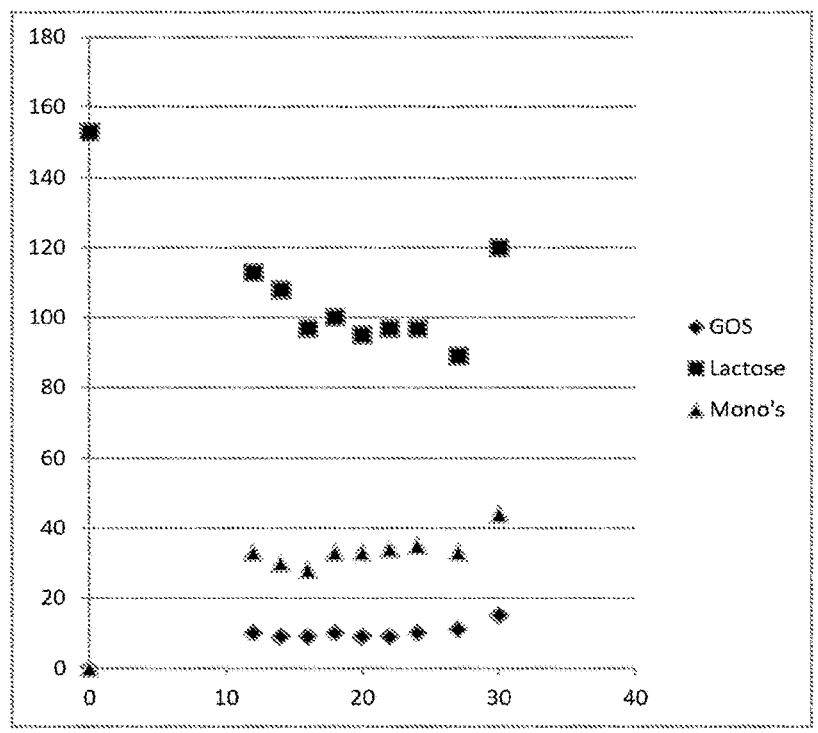
GOS%
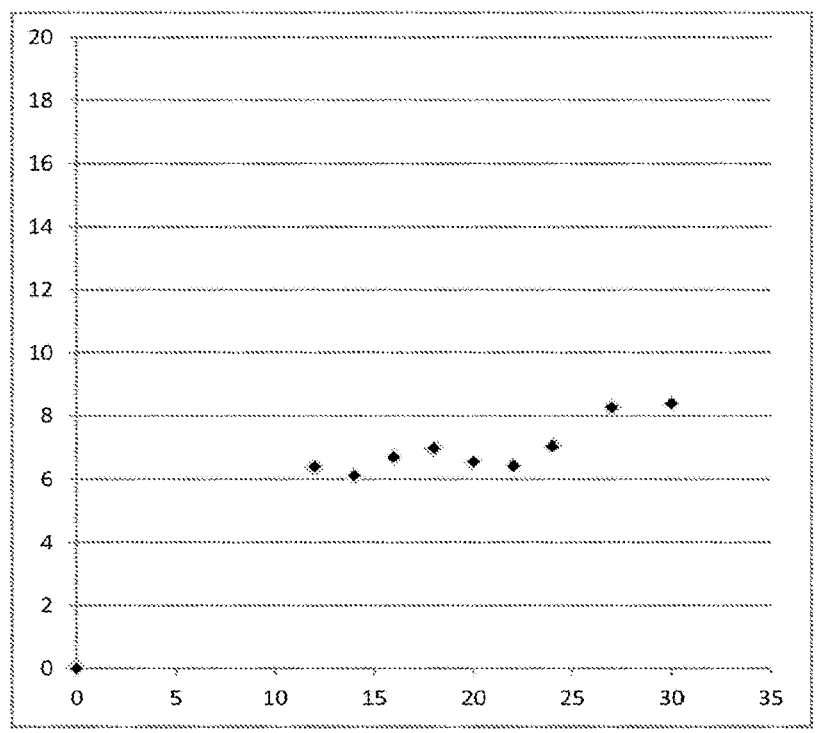

Figure 10
Sugars
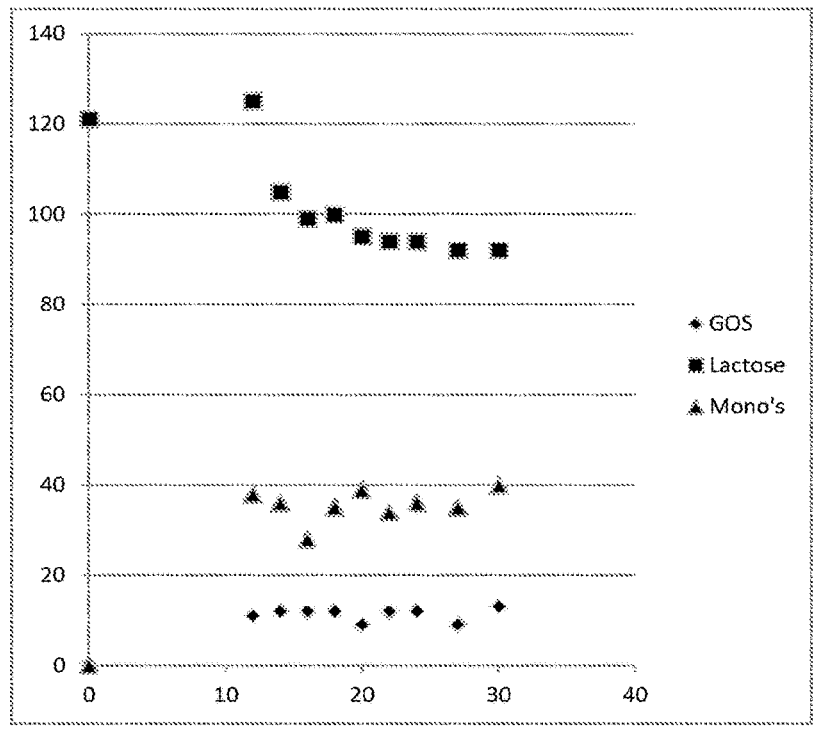
GOS%
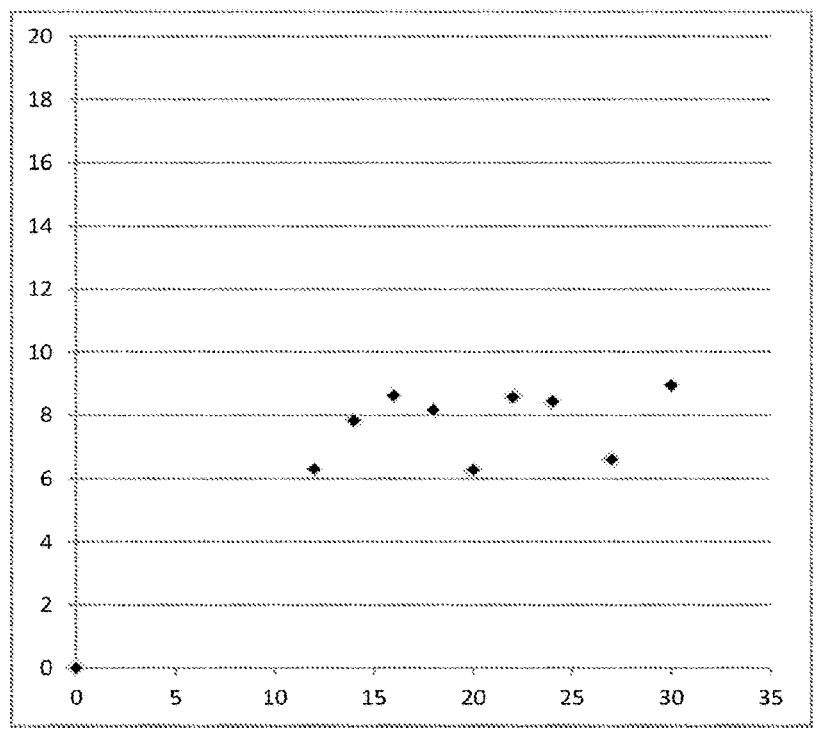

Figure 11
Sugars
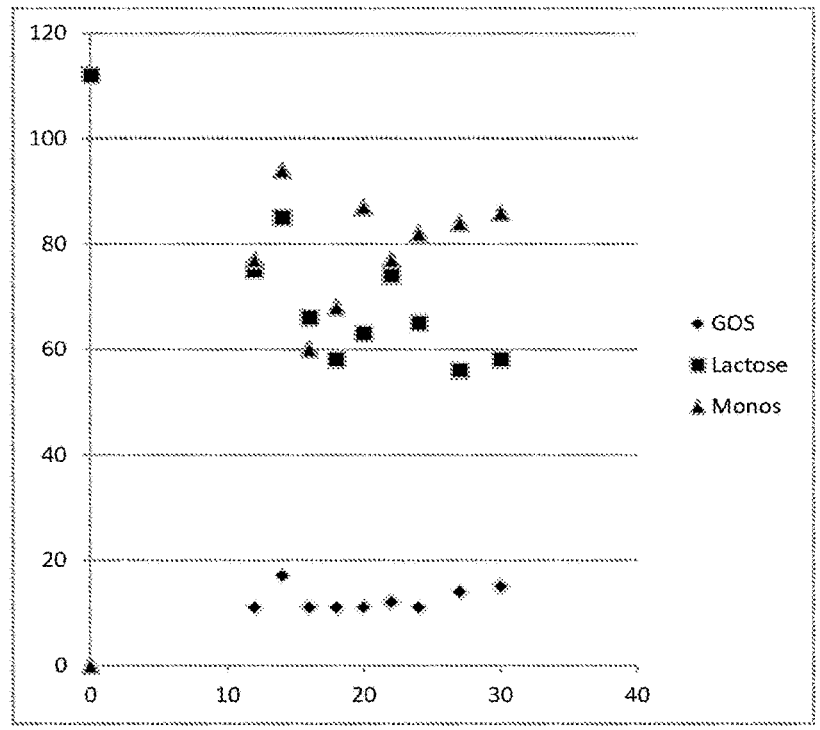
GOS%
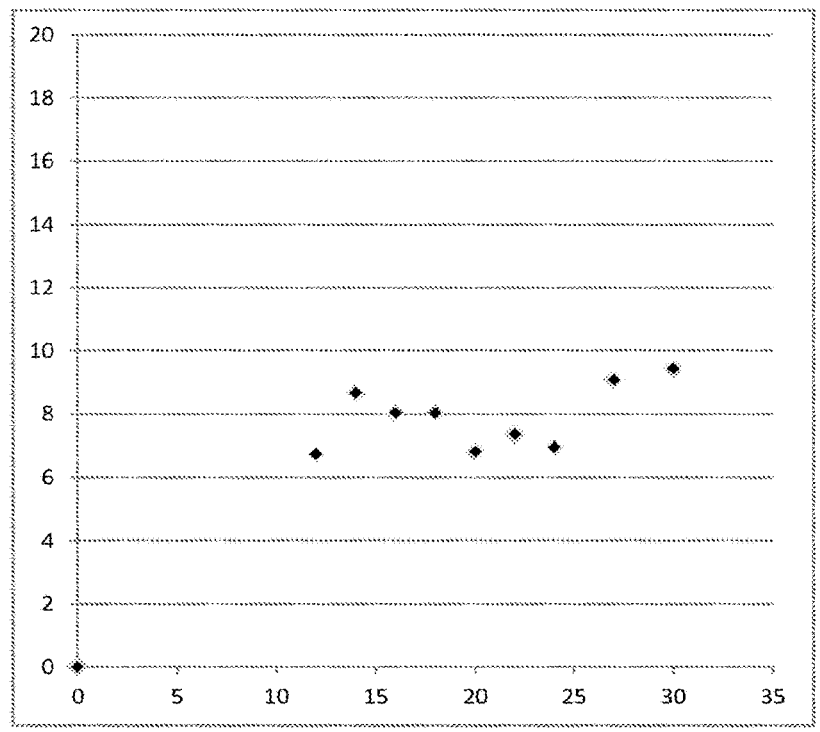

Figure 12
Sugars
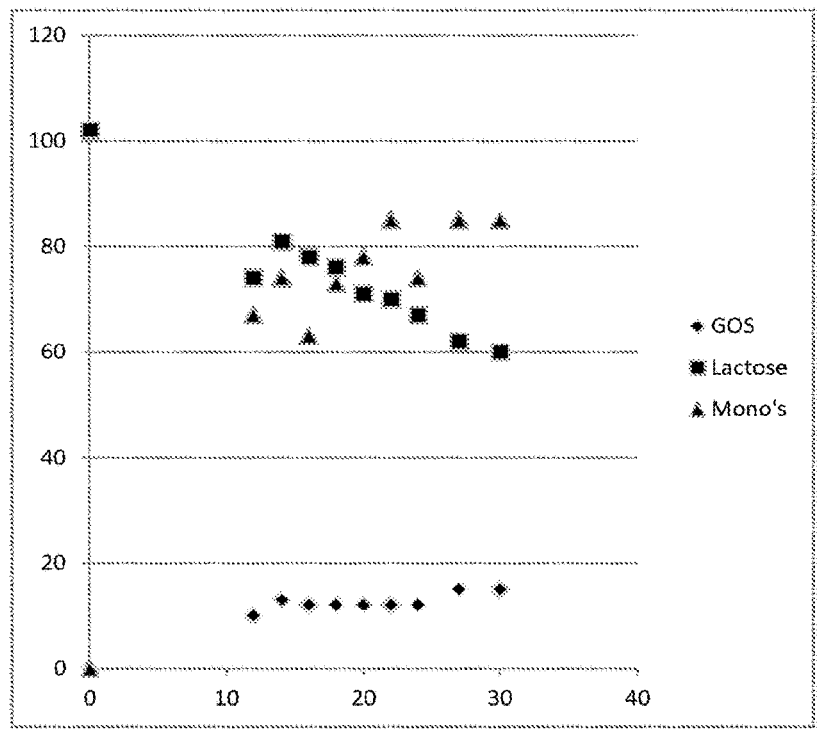
GOS%
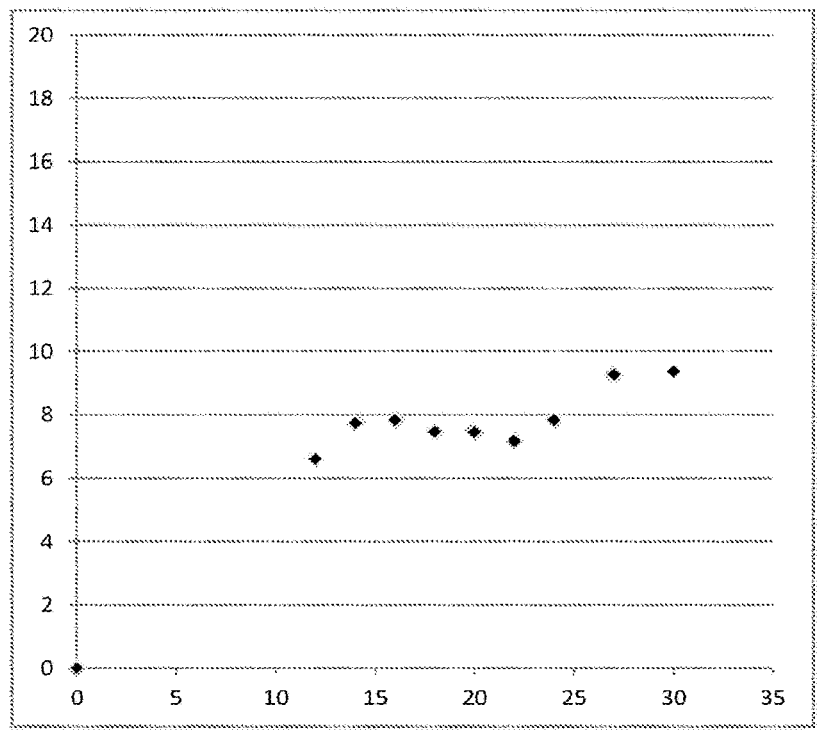

Figure 13
Sugars
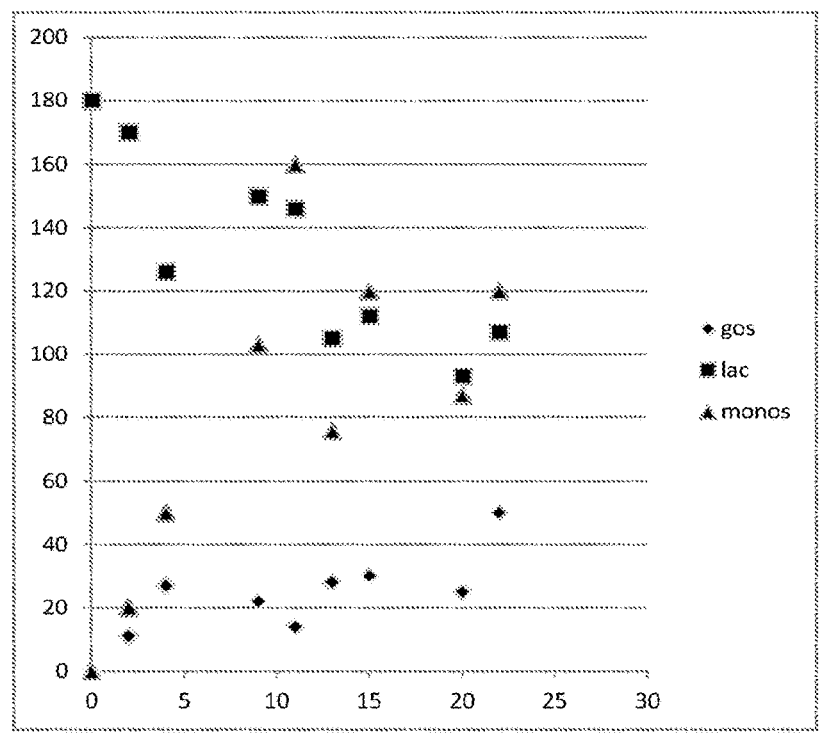
GOS%
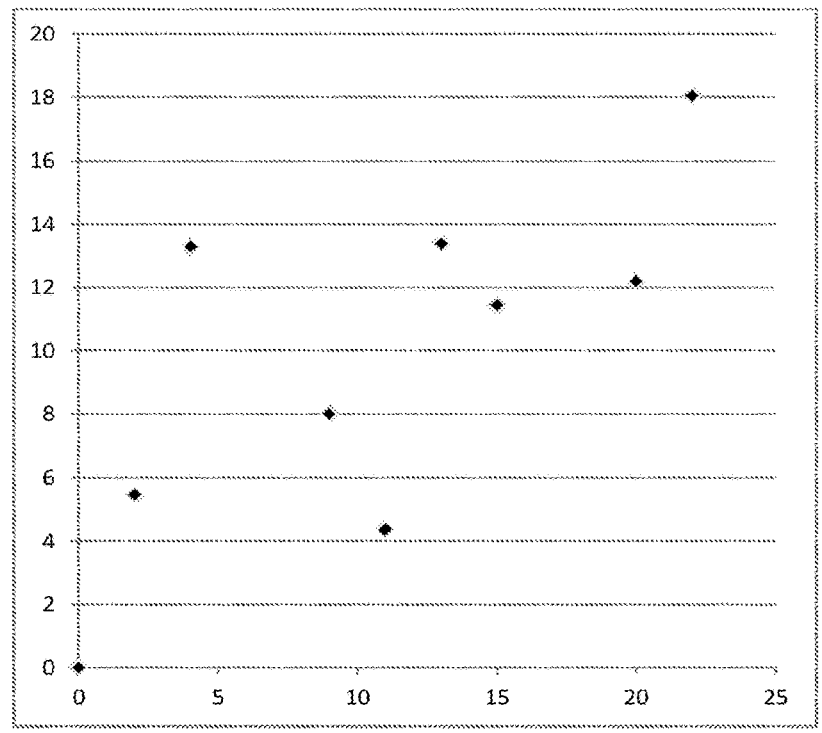

Figure 14
Sugars
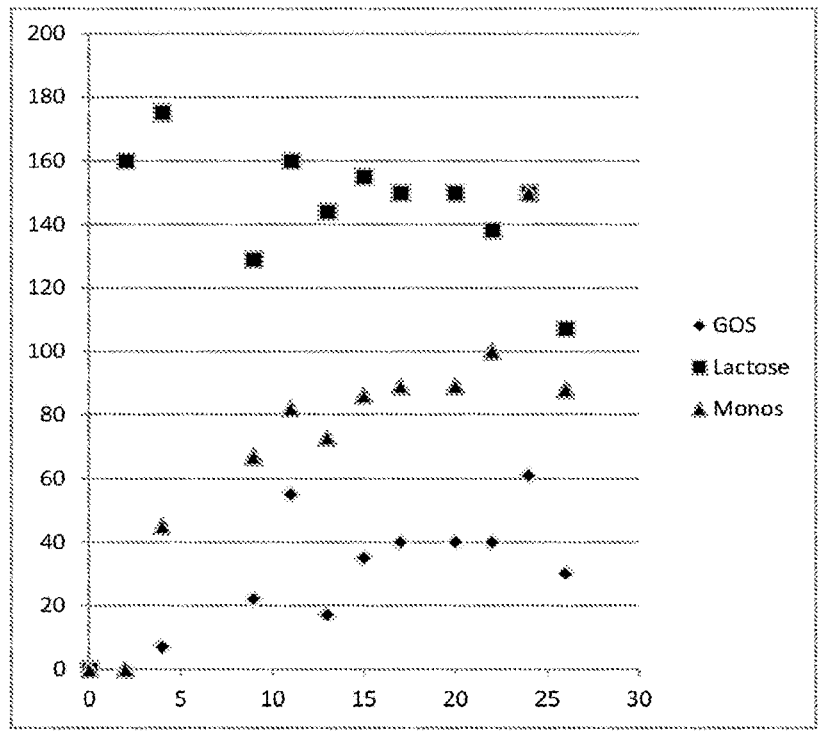
GOS %
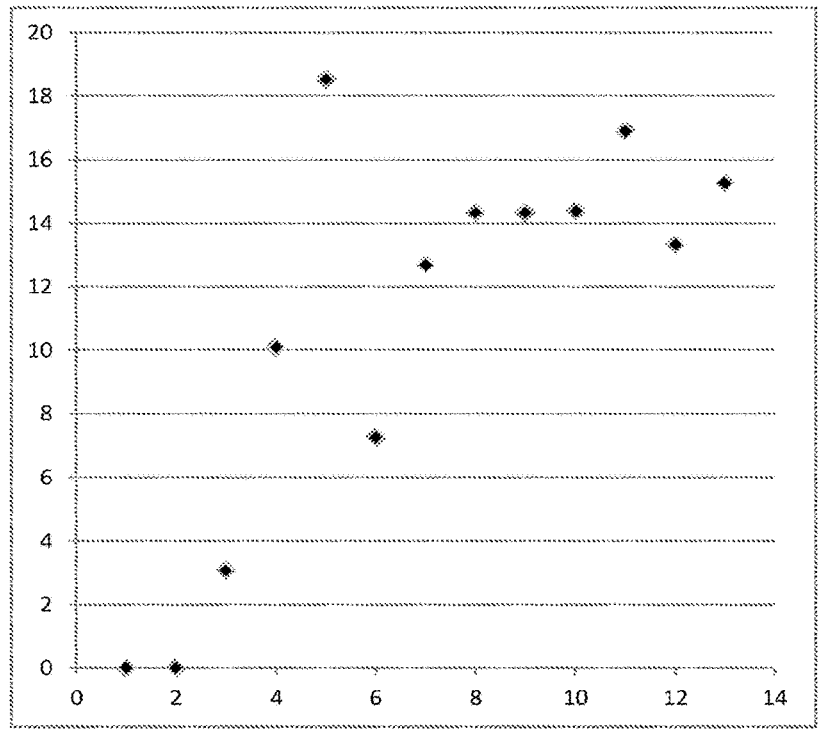

Figure 15
Sugars
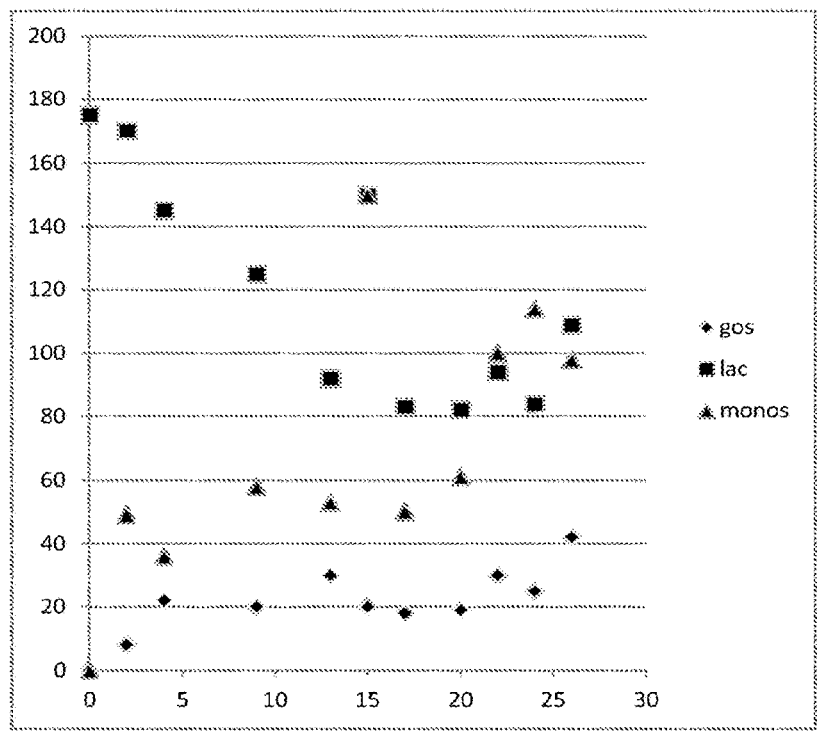
GOS%
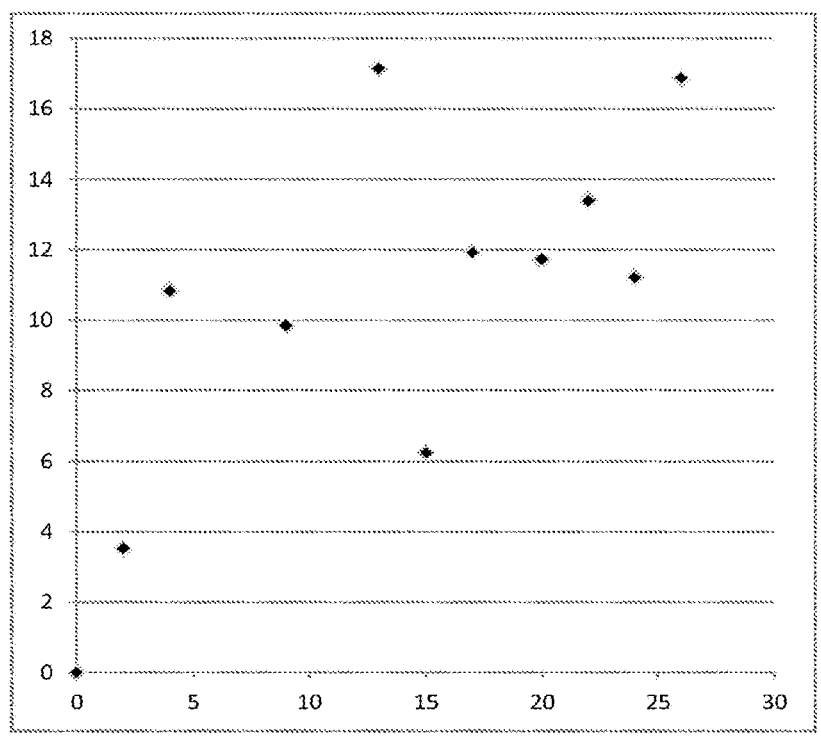

Figure 16
Sugars
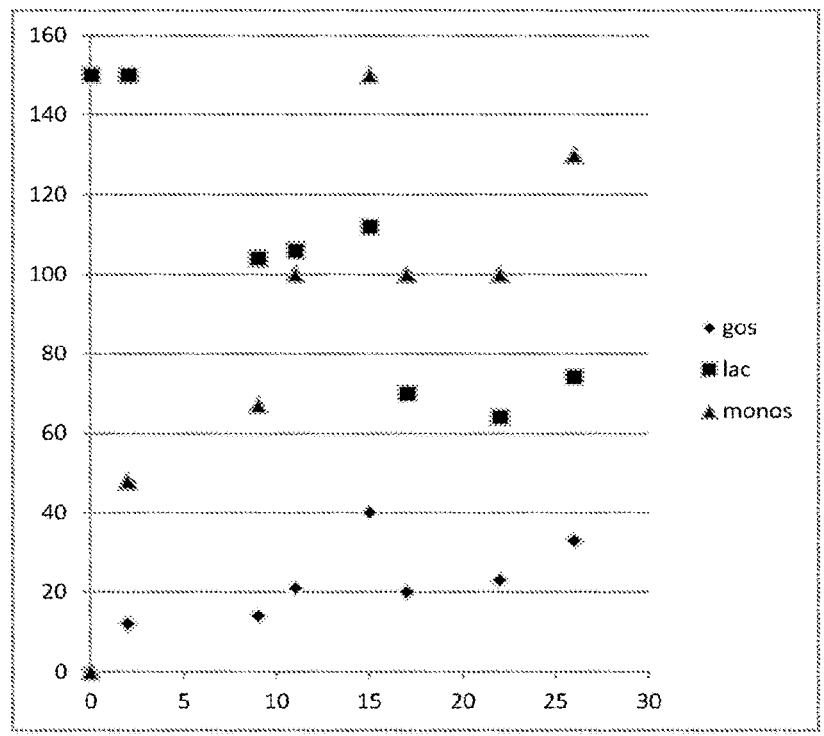
GOS%
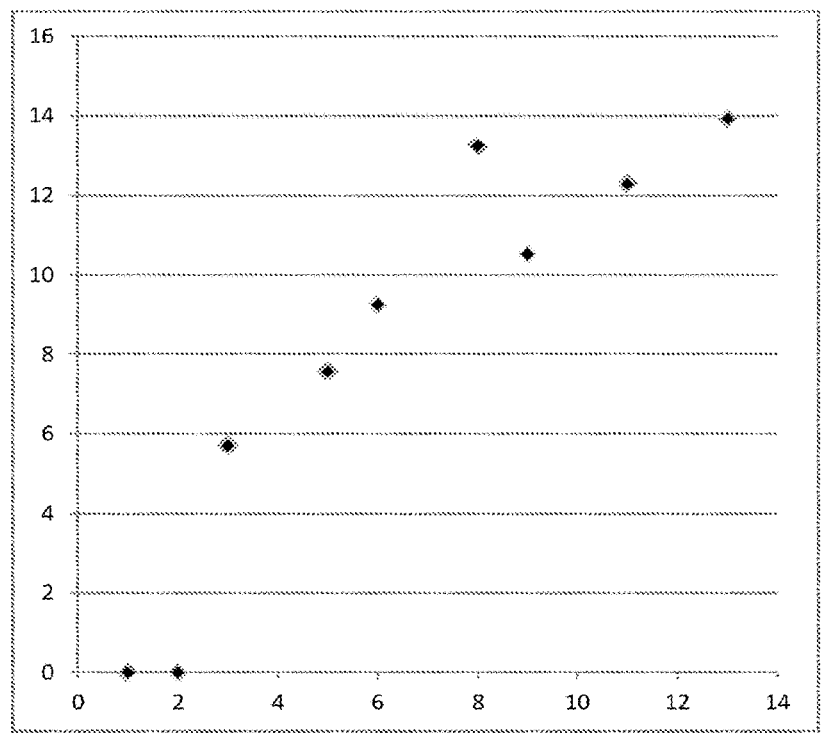

COMPOSITION AND METHODS OF SCREENING

CROSS REFERENCE TO RELATED APPLICATIONS

This application is a continuation of U.S. application Ser. No. 15/034,420, filed on May 4, 2016, which is a U.S. National Phase of PCT/GB2014/053303, filed Nov. 5, 2014, which claims priority to Great Britain Application No. 1319539.1, filed Nov. 5, 2013, each of which is incorporated herein by reference in its entirety.

TECHNICAL FIELD OF THE INVENTION

The invention relates to a prebiotic composition which is specific for the growth of a desired probiotic bacterial strain.

BACKGROUND TO THE INVENTION

Probiotics are bacteria which confer health benefits to a host. Typically, cultures of probiotic bacterial strains are consumed or administered to individuals in order to supplement the naturally occurring bacteria population of the gut. A number of health benefits have been associated with probiotics, including reducing the incidence of cancer, diarrhoea and irritable bowel syndrome to name a few. Preliminary studies also indicate that probiotics can be useful in reducing serum levels of cholesterol and blood pressure and help modulate diabetes.

Lactobacilli are common probiotics in dairy products and make up approximately 75% of probiotics currently sold. However, it has been estimated that only 2% of Lactobacilli dose survives be effective in the gut.

Prebiotics are dietary ingredients which can selectively enhance beneficial indigenous gut microbiota, such as lactobacilli or bifidobacteria, and are finding much increased application into the food sector. Prebiotics are non-digestible food ingredients that are selectively metabolised by colonic bacteria which contribute to improved health. As such, their use can promote beneficial changes within the indigenous gut microbial milieu and they can therefore help survivability of probiotics. They are distinct from most dietary fibres like pectin, celluloses, xylan, which are not selectively metabolised in the gut. Criteria for classification as a prebiotic is that it must resist gastric acidity, hydrolysis by mammalian enzymes and gastrointestinal absorption, it is fermented by intestinal microflora and selectively stimulates the growth and/or activity of intestinal bacteria associated with health and well-being.

Fructo-oligosaccharides (FOS, inulin and oligofructose) and galactooligosaccharides (GOS) have been demonstrated to fulfil the criteria for prebiotic classification repeatedly in human intervention studies. Currently, no prebiotic for Lactobacilli exists.

It is an object of the present invention to provide a prebiotic composition which allows for the specific growth of a given probiotic bacteria. It would also be desirable if the prebiotic targeted a beneficial strain of prebiotic such as a Lactobacilli. A yet further object of the present invention is to provide a screening method to identify and produce prebiotic compositions which are selective for certain probiotic bacterial strains.

SUMMARY OF THE INVENTION

In accordance with a first aspect of the present invention, there is provided a prebiotic composition comprising a microbially produced oligosaccharide, wherein the oligosaccharide is characterised by being selective for a pre-determined probiotic bacterial strain and also capable of being produced by the pre-determined probiotic bacterial strain by reverse enzyme reaction.

The enzyme may comprise a saccharolytic enzyme. Such an enzyme may be one selected from one of following: β-galactosidases, α-galactosidases, α- and β-glucosidases, α-mannosidases, or β-xylosidases.

The prebiotic composition may comprise galacto oligosaccharide (GOS).

The pre-determined bacterial strain preferably comprises a Lactobacilli and may comprise a strain selected from: *Lactobacillus acidophilus, Lactobacillus reuteri, Lactobacillus rhamnosus, Lactobacillus plantarum, Lactobacillus-delbrueckii* ssp. *bulgaricus, Lactobacillus casei, Lactobacillus salivarius, Lactobacillus salivarius* ssp. *salivarius, Lactobacillus fermentum* or *Lactobacillus helveticus*. It is preferred that the GOS form is substantially the same as the form produced by reverse β-galactosidase reaction of the bacterial strain.

The prebiotic composition will preferably be present in the composition in an effective amount so as to elicit a change in the proportions of the desirable indigenous gut microbiota and in particular the preferred probiotic bacterial strain. Higher amounts may be utilised if change in the microbiota is required quickly or if the composition is being used to help seed the gut with a new bacterial strain not currently present.

The prebiotic composition may be encapsulated. Many encapsulation techniques will be apparent to the skilled addressee and the one employed will be tailored to the required stability of the prebiotic growth medium during digestive transit.

The prebiotic composition may further comprise an excipient or carrier compound to enable it to pass through the gastrointestinal environment of the body and be efficiently delivered to, and released in the lower gut. The prebiotic may be concentrated and/or freeze dried. The composition may be in a number of formats, such as a drinkable liquid and/or powder which can be mixed with a solid or liquid food stuff.

The prebiotic composition may be combined with one or more active ingredients, such as vitamins, minerals, phytochemicals, antioxidants, and combinations thereof.

Vitamins may include fat soluble vitamins such as vitamin A, vitamin D, vitamin E, and vitamin and combinations thereof. In some embodiments, vitamins can include water soluble vitamins such as vitamin C (ascorbic acid), the B vitamins (thiamine or B 1, riboflavoin or B25 niacin or B3, pyridoxine or B6, folic acid or B9, cyanocobalimin or B12, pantothenic acid, biotin), and combinations thereof.

Minerals may include but are not limited to sodium, magnesium, chromium, iodine, iron, manganese, calcium, copper, fluoride, potassium, phosphorous, molybdenum, selenium, zinc, and combinations thereof.

Antioxidants may include but are not limited to ascorbic acid, citric acid, rosemary oil, vitamin A, vitamin E, vitamin E phosphate, tocopherols, di-alpha-tocopheryl phosphate, tocotrienols, alpha lipoic acid, dihydrolipoic acid, xanthophylls, beta cryptoxanthin, lycopene, lutein, zeaxanthin, astaxanthin, beta-carotene, carotenes, mixed carotenoids, polyphenols, flavonoids, and combinations thereof.

Phytochemicals may include but are not limited to cartotenoids, chlorophyll, chlorophyllin, fiber, flavanoids, anthocyamns, cyaniding, delphinidin, malvidin, pelargonidin, peonidin, petunidin, flavanols, catechin, epicatechin, epigallocatechin, epigailocatechingallate, theaflavins, thearubigins, proanthocyanins, flavonols, quercetin, kaempferol, myricetin, isorhamnetin, flavononeshesperetin, naringenin, eriodictyol, tangeretin, flavones, apigenin, luteolin, lignans, phytoestrogens, resveratrol, isoflavones, daidzein, genistein, glycitein, soy isoflavones, and combinations thereof.

In accordance with a further aspect of the present invention, there is provided a prebiotic composition for use in the management of cholesterol or the treatment of high cholesterol. Alternatively or additionally, the composition may be for use in the management or treatment of a metabolic syndrome, weight management or obesity or diabetes. The composition comprising a microbially produced oligosaccharide, wherein the oligosaccharide is characterised by being selective for a pre-determined probiotic bacterial strain and also capable of being produced by the pre-determined probiotic bacterial strain by reverse enzyme reaction a prebiotic composition as herein above described for use as a medicament or pharmaceutical and/or a dietary supplement.

In accordance with a further aspect of the present invention, there is provided a prebiotic composition for the treatment of high cholesterol, a metabolic syndrome, obesity or diabetes, the composition comprising a microbially produced oligosaccharide, wherein the oligosaccharide is characterised by being selective for a pre-determined probiotic bacterial strain and also capable of being produced by the pre-determined probiotic bacterial strain by reverse enzyme reaction.

In a yet further aspect of the present invention, there is provided a use of a prebiotic composition, in the manufacture of a medicament for the treatment of high cholesterol, a metabolic syndrome, obesity or diabetes, the composition comprising a microbially produced oligosaccharide, wherein the oligosaccharide is characterised by being selective for a pre-determined probiotic bacterial strain and also capable of being produced by the pre-determined probiotic bacterial strain by reverse enzyme reaction.

It will be apparent to the skilled addressee that the features of the prebiotic as described in the first aspect of the invention will also be applicable and interchangeable for the composition for the management of cholesterol.

Alternative (or additionally) to a pharmaceutical or medicament, the composition may be used as a dietary supplement, a nutraceutical or a functional food. A yet further aspect of the present invention may be a prebiotic composition for a dietary supplement, a nutraceutical or a functional food, the composition comprising a microbially produced oligosaccharide, wherein the oligosaccharide is characterised by being selective for a pre-determined probiotic bacterial strain and also capable of being produced by the pre-determined probiotic bacterial strain by reverse enzyme reaction.

It will again be apparent to the skilled addressee that the features of the prebiotic in connection with the first aspect of the invention will also be applicable and interchangeable for the composition for a dietary supplement, a nutraceutical or a functional food.

Furthermore, the composition could be incorporated into an existing food, such as yoghurt or as a powder which can be easily blended with foodstuffs or made into a liquid drink.

In accordance with another aspect of the present invention, there is provided a method of screening a composition which is suitable for use as a prebiotic comprising the steps;
(a) assembling a panel of probiotic bacterial strains;
(b) selecting a strain found to have oligosaccharide activity;
(c) inducing the selected probiotic strain to produce a oligosaccharide prebiotic composition by reverse enzyme reaction; and
(d) isolating the oligosaccharide prebiotic composition.

The method may further comprise:
(e) assessing growth and/or survivability of the selected probiotic bacteria strain using the isolated oligosaccharide prebiotic composition.

By utilising reverse enzyme reaction in the probiotic bacterial strain to produce a prebiotic which is specific to the probiotic, the subsequent use of the prebiotic allows for greater specificity of growth promotion for the desired probiotic strain at the expense of other bacterial strains.

It is preferred that the oligosaccharide comprises GOS.

The method may be used in the identification and production of a prebiotic composition as herein above described.

In accordance with yet a further aspect of the present invention, there is provided a method of screening for a synbiotic formulation comprising the steps:
(a) assembling a panel of probiotic bacterial strains;
(b) selecting strains found to have oligosaccharide activity;
(c) inducing the selected probiotic strains to produce a oligosaccharide prebiotic composition by reverse enzyme reaction;
(d) isolating the oligosaccharide prebiotic compositions for each selected strain;
(e) combining each selected strain and corresponding isolated oligosaccharide prebiotic composition in a formulation; and
(f) assessing the improved growth and/or survivability of the selected probiotic bacterial strain for each formulation in a gut model and identifying the formulation showing improved growth and/or survivability.

The gut model may comprise an in vivo method of investigating the gut microbial flora of an individual before and after administration of a given formulation. In the alternative, the gut model may comprise an in vitro method which substantially mimics the conditions of the gut.

It will be apparent to the skilled addressee that the features of the prebiotic in connection with the first aspect of the invention will also be the desired attributes of the composition forming part of the screened formulation.

DETAILED DESCRIPTION OF THE INVENTION

Embodiments of the present invention will now be described, by way of example only, in which:

FIG. 1A is a graph of bacterial count over time using 0.1% lactose as a growth medium for *L. plantarum;*

FIG. 1B is a graph of bacterial count over time using 0.1% lactose as a growth medium for *L. casei;*

FIG. 1C is a graph of bacterial count over time using 0.1% lactose as a growth medium for *L. salivarius;*

FIG. 1D is a graph of bacterial count over time using 0.1% lactose as a growth medium for *L. fermentum;*

FIG. 1E is a graph of bacterial count over time using 0.1% lactose as a growth medium for *L. rhanmosus;*

FIG. 1F is a graph of bacterial count over time using 0.1% lactose as a growth medium for *L. delbrueckii;*

FIG. 2A is a graph of bacterial count over time using 5% lactose as a growth medium for *L. plantarum;*

FIG. 2B is a graph of bacterial count over e using 5% lactose as a growth medium for *L. casei;*

FIG. 2C is a graph of bacterial count over time using 5% lactose as a growth medium for *L. salivarius*;

FIG. 2D is a graph of bacterial count over time using 5% lactose as a growth medium for *L. delbrueckii*;

FIG. 2E is a graph of bacterial count over time using 5% lactose as a growth medium for *L. rhanmosus*;

FIG. 2F is a graph of bacterial count over time using 5% lactose as a growth medium for *L. acidophilus*;

FIG. 2G is a graph of bacterial count over time using 5% lactose as a growth medium for *L. helveticus*;

FIGS. 9 & 10 shows graphs of the quantity of Sugars (GOS, Lactose and Monosaccharides) and GOS % over time for *L. fermentum* ATCC 11976;

FIGS. 11 & 12 shows graphs of he quantity of Sugars (GOS, Lactose and Monosaccharides) and GOS % over time for *L. fermentum* NCIMB 30226;

FIG. 13 shows graphs of the quantity of Sugars (GOS, Lactose and Monosaccharides) and GOS % over time for 18 U. *L. fermentum* ATCC 11976;

FIG. 14 shows graphs of the quantity of Sugars (GOS, Lactose and Monosaccharides) and GOS % over time for 18 U. *L. fermentum* NCIMB 30226;

FIG. 15 shows graphs of the quantity of Sugars (GOS, Lactose and Monosaccharides) and GOS % over time for 30 U. *L. fermentum* ATCC 11976;

FIG. 16 shows graphs of the quantity of Sugars (GOS, Lactose and Monosaccharides) and GOS % over time for 30 U. *L. fermentum* NCIMB 30226;

Figure 3:
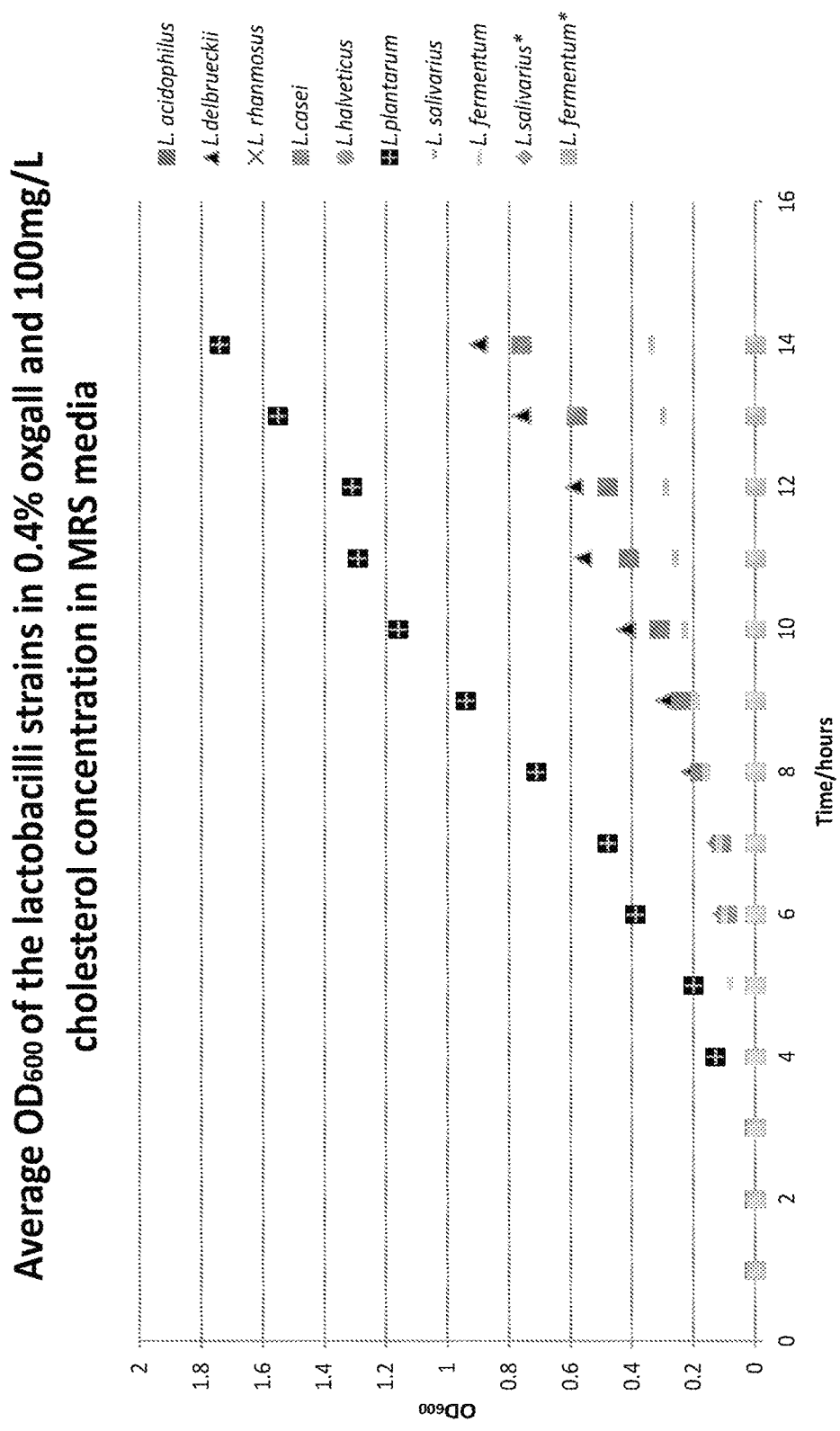
FIG. 3 is a graph showing the results of different bacterial strains over 14 hours ($OD_{600}$ measured every hour) in 0.4% oxgall and 100 mg/L cholesterol concentration in MRS media.

Mechanistically glycosidases are all transferases that use water as their preferred acceptor molecule. Under appropriate circumstances, however, such as high concentrations of substrate carbohydrate, these enzymes will transfer monosaccharide moieties from the substrate (acting as glycosyl donor) to other substrate or non-substrate carbohydrates (acting as glycosyl acceptor). Typically, the products of these reactions are complex mixtures containing all possible glycosidic linkages but in differing amounts. As the reactions are kinetically controlled, the linkage profile synthesised should map onto the rate constants for hydrolysis of those linkages by the producing enzyme. Consequently the oligosaccharides may be more readily metabolised by the producing organisms than by others in the gastrointestinal ecosystem. This approach has shown promise in laboratory testing.

It is possible, however in many enzyme synthesis reactions to include other carbohydrates which will act as acceptors in addition to the lactose. In this way, novel mixtures containing novel structures could be built up.

Probiotic species such as lactobacilli and bifidobacteria are highly saccharolytic and they frequently produce a range of glycosidase enzymes. These enzymes may have transfer activity and be able to synthesise oligosaccharides. This activity is widely reported for β-galactosidases but has not been as intensively studied for other enzymes such as α-galactosidases, α- and β-glucosidases, α-mannosidases, or β-xylosidases. It is also possible to synthesise oligosaccharides using sucrose dependant glycosyltransferases. These transfer either the fructose or glucose moiety from sucrose to sucrose acceptors and build up long polysaccharide chains. In the presence of suitable acceptors, however, they frequently synthesise hetero-oligosaccharides. This has been shown to occur with dextransucrase and alternansucrase and may also occur with laevansucrase.

The experiments sought to explore a strategy to use the products of one synthesis reaction as acceptors in a subsequent reaction. If a probiotic produces a β-galactosidase and a laevan sucrase, for instance, an enzyme extract could be used to synthesise galactooligosaccharides. This product mixture could then be used with the same extract and sucrose as glycosyl donor to bring about the synthesis of fructans—many of which would be built up on the galactooligosaccharides which would act as acceptors. In this way novel complex mixtures could be produced that should have a highly tailored fermentation by the producing organism.

The basis of the present experiments was to reversibly use β-galactosidases in microorganisms so as to produce a novel GOS. Ordinarily, β-galactosidases would digest lactose. However, by changing the reaction conditions, in terms of substrate and temperature, the enzyme acts reversibly and generates an oligosaccharide version of the lactose (GOS).

Lactobacilli are more frequently used as probiotics than are bifidobacteria, yet no prebiotic selective to lactobacilli exists. As these probiotics also harbour β-galactosidase activity, the experiments induced the production of GOS which was specific to these probiotics. The metabolism of prebiotics like GOS are species specific (as evidenced by Bi-Immuno and Bifidobacteria), so a Lactobacilli GOS has the potentially enhance the growth, survivability, and health benefits of lactobacilli.

The experiments undertaken were as follows;
1. Assemble and test a range of probiotic lactobacilli for their capacity to generate GOS and measuring β-galactosidase activities;
2. Generate a prebiotic GOS using the reverse enzyme procedure;
3. Scale up of the novel molecule to allow in vitro testing;
4. Compare survival and growth of lactobacilli in the absence and presence of the prebiotic in a series of 'gut model' experiments that test the probiotics and synbiotics;
5. Assess the possibility for using GOS as encapsulation material for the lactobacilli; and
6. Test delivery properties of the encapsulation material.

The bacterial strains initially investigated during the first stage of the experiments are shown below in Table 1:

TABLE 1

| Strain | Number | Origin |
|---|---|---|
| Lactobacillus acidophilus | NCIMB 30184 | Human |
| Lactobacillus rhamnosus | NCIMB 30188 | Human |
| Lactobacillus plantarum | NCIMB 30187 | Pickled cabbage |
| Lactobacillus delbrueckii ssp. bulgaricus | NCIMB 30186 | Yogurt |
| Lactobacillus casei | NCIMB 30185 | Cheese |
| Lactobacillus salivarius ssp. salivarius | NCIMB 30225 | Human |
| Lactobacillus fermentum | NCIMB 30226 | Dairy |
| Lacobacillus helveticus | NCIMB30224 | Dairy |
| Lactobacillus fermentum | ATCC11976 | Human |
| Lactobacillus salivarius | ATCC 11741 | Human |

Bacterial growth curve determination was undertaken by sampling cultures at 0 h, 3 h, 5 h, 8 and 24 h intervals using a 100 μL of dilution series of culture in 900 μL PBS. 20 μL of each series was spread onto a jar and with a negative control and growth assessed.

Bacterial count of several of the strains was assessed by using 0.1% lactose as the growth medium. FIGS. 1A-1F show that bacterial count over time using 0.1% lactose as a growth medium for L. plantarum, L. casei, L. salivarius, L. fermentum, L. rhanmosus, and L. delbrueckii all resulted in a steady growth curve from approximately 6.5 log 10 CFU/ml to just over 9.5 log 10 CFU/ml at around 13 hours and growth tailed off as it did not increase by 25 hours.

Bacterial count of several of the strains was assessed by using 5% lactose as the growth medium. FIGS. 2A-2G show the bacterial count over time using 5% lactose as a growth medium for L. plantarum, L. casei, L. salivadus, L. delbrueckii, L. rhanmosus, L. acidophilus and L. helveticus. Again, all resulted in a steady growth curve from approximately 6.5 log 10 CFU/ml to just over 9.5 log 10 CFU/ml at around 13 hours and growth was then flat as it did not increase by 25 hours.

Cholesterol was then included in the culture medium of the bacterial strains and each strain tested for quantity of cholesterol after incubation.

The cholesterol assay used relies on the following formula:

$$\% \text{ cholesterol} \times \text{dry weight } (g)^{-1} = (B - T/B \times 100)/W$$

Where B=cholesterol content in the uninoculated control mg/l$^{-1}$, T=cholesterol in culture medium mg/l$^{-1}$ and W=cells (dry weight g after 12 h of inc).

The pellet weight of the culture was measured independently of the supernanent and the spent broth (evaporated residues) also measured. The cholesterol assay was run in triplicate in several runs.

FIG. 3 shows the growth of different bacterial strains over 14 hours (OD$_{600}$ measured every hour) in 0.4% oxgall and 100 mg/L cholesterol concentration in MRS media and shows that some bacterial strains were much more effective at growing in this media. L. Planatarum showed the best growth profile, followed by L. delbrueckii, L. casei and L. fermentum. FIG. 3 shows the growth of different bacterial strains over 12 hours (OD$_{600}$ measured every hour) in 0.4% oxgall and 100 mg/L cholesterol concentration in MRS media and shows that some bacterial strains were much more effective at growing in this media. L. planatarum showed the best growth profile, followed by L. delbrueckii, L. casei and L. fermentum.

Figure 4:
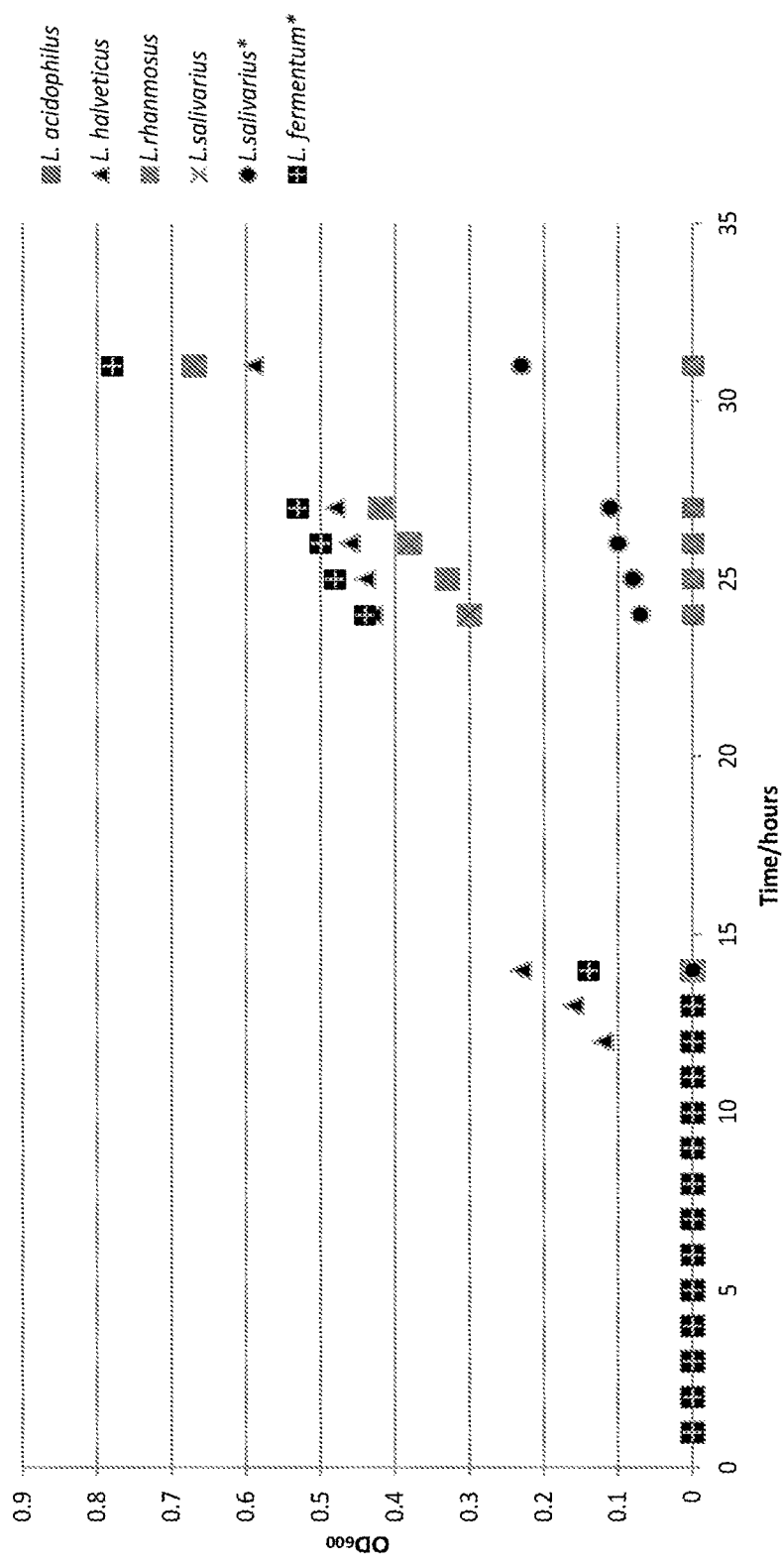
FIG. 4 is a graph showing the results of different bacterial strains over 2 days prior to testing ($OD_{600}$ measured every hour) in 0.4% oxgall and 100 mg/L cholesterol concentration in MRS media.

FIG. 4 is a graph showing the results of different bacterial strains over 2 days prior to testing (OD$_{600}$ measured every hour) in 0.4% oxgall and 100 mg/L cholesterol concentration in MRS media. L. fermentum showed the best growth profile, followed by L. rhanmosus, L. halveticus, L. halveticus and L. salivarius.

Direct plate assay tests were then conducted on the strains to further measure cholesterol activity. Resting cell Bile Salt Hydrolase (BSH) activity was measured to assess the release of amino acids from hydrolysis of conjugated bile acids. Bile salt deconjugation (based upon the release of free cholic acid) was measured and finally co-precipitation of cholesterol with deconjugated bile assessed. Table 2 below shows the results of the direct plate assay.

TABLE 2

| Bacteria | 1$^{st}$ run | 2$^{nd}$ run | 3$^{rd}$ run |
|---|---|---|---|
| L. casei | Y | Y | Y |
| L. delbrueckii | Y | Y | Y |
| L. acidophilus | Y | Y | Y |
| L. fermentum | X | Y | Y |
| L. salivarius | X | X | X |
| L. halveticus | Y | X | X |
| L. rhamnosus | X | X | X |
| L. plantarum | X | Y | Y |
| L. salivarius* | X | X | X |
| L. fermentum* | X | X | Y |

It can be seen that L. casei, L. delbrueckii and L. acidophilus all had reliable BSH activity.

By comparing the results of the strains being able to grow in media containing cholesterol and those strains having BSH activity L. casei and L. delbrueckii appear to be suitable candidates for producing and identifying a specific prebiotic GOS.

The GOS prebiotic generated by a specific strain has optimised metabolism not just to produce the GOS, but also to metabolise it (as its generated from a reverse enzyme procedure). The GOS can therefore be incorporated with the probiotic into a synbiotic that would create a highly selective environment for the probiotic. As a probiotic can have a specific health benefits then a synbiotic formula which is tailored to a specific health benefit can be generated.

A screening method for identifying and formulating a synbiotic composition in accordance with an aspect of the invention follows the steps of:

(a) Identifying health need;
(b) Identifying key interjection points for probiotic action e.g BSH activity, cholesterol assimilation & heart disease;
(c) Screening probiotic library using high throughput screening methodology;
(d) Identifying strains with potential activity & health benefits;
(e) Optimising expression of activity using fermentation processes;
(f) Screening strains for beta galactosidase activity;
(g) Generating a novel GOS;
(h) Scaling up to allow in vitro testing;
(i) Comparing survival and growth of the probiotic in the absence and presence of the prebiotic using in vitro plate assays and gut model. If strain characterised then use molecular methodologies to study population changes over time. This will see if affect due to increasing number or increasing activity; and
(j) Combining pre & probiotic to explore effect of combined pre & probiotic.

Evaluation of Anaerobic Utilisation of Novel L. reuteri GOS

In these experiments, anaerobic cultures were tested to evaluate the in vitro utilisation of a novel Lactobacillus reuteri galactooligosaccharide by monitoring the populations of gut bacterial groups at 24 hours using fluorescent in situ hybridisation, and short-chain fatty acid (SOFA). Fructooligosaccharides (FOS), melibiose and raffinose were used as reference carbohydrates. The table below shows the results of these experiments.

| Group | Inoculum | Melibiose | | Raffinose | | FOS | | GOS | | GOS + *L. acidophilus* | | GOS + *L. reuterri* | |
|---|---|---|---|---|---|---|---|---|---|---|---|---|---|
| | | 24 | 24 hr % change | 24 | 24 hr % change | 24 | 24 hr % change | 24 | 24 hr % change | 24 | 24 hr % change | 24 | 24 hr % change |
| Total count | 8.84 | 9.14 | 103% | 9.19 | 104% | 9.2 | 104% | 9.12 | 103% | 9.55 | 108% | 9.34 | 106% |
| Bifidobacteria | 6.85 | 7.33 | 107% | 7.69 | 112% | 7.47 | 109% | 7.69 | 112% | 7.83 | 114% | 8.19 | 120% |
| *Bacteroides* | 7.98 | 7.9 | 99% | 8.08 | 101% | 8.08 | 101% | 7.95 | 100% | 8.01 | 100% | 7.89 | 99% |
| Lactobacilli | 7.15 | 7.43 | 104% | 7.45 | 104% | 7.32 | 102% | 7.69 | 108% | 7.67 | 107% | 7.73 | 108% |
| Clostridia | 7.55 | 7.65 | 101% | 7.81 | 103% | 8 | 106% | 7.23 | 96% | 7.48 | 99% | 7.2 | 95% |
| *E. coli* | 8.14 | *7.66* | *94%* | 8.03 | 99% | 7.85 | *96%* | 8.04 | 99% | 8.24 | 101% | 7.96 | 98% |
| Eubacteria | 8.06 | 7.84 | 97% | 8.69 | 108% | 8.27 | 103% | *7.75* | *96%* | 8.16 | 101% | 8.28 | 103% |

(Key: BOLD = Significant Increase; Italics = Significant Decrease)

The results show the *Lactobacillus reuterri* GOS showed a significant increase in bifidobacteria and lactobacilli population numbers exhibiting a prebiotic affect. In addition, the GOS increased the growth rate of lactobacilli by 108%, more than any other sugar suggesting a genus specificity. Addition of a strain of *Lactobacillus reuterri* increased the prebiotic affect, increasing the *bifidobacterium* population by 120%.

This suggests that the addition of a GOS producing organism to the GOS produced by that organism had a greater effect on the gut microflora population than the GOS alone.

Lactobacilli β-Galactosidase Screening Assay

Figure 5A:
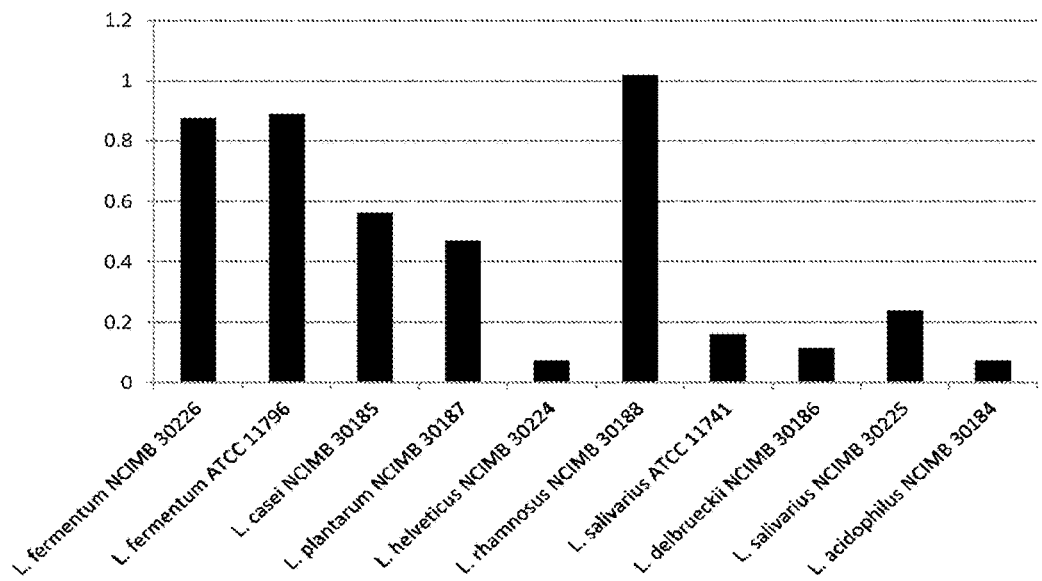
FIG. 5A-5C are graphs show the results of a range of lactobacilli species which were screened for β-galactosidase activity measured at $OD_{420}$ in A MRS broth, B 1% lactose basal media and C 5% lactose basal media.
Figure 5B:
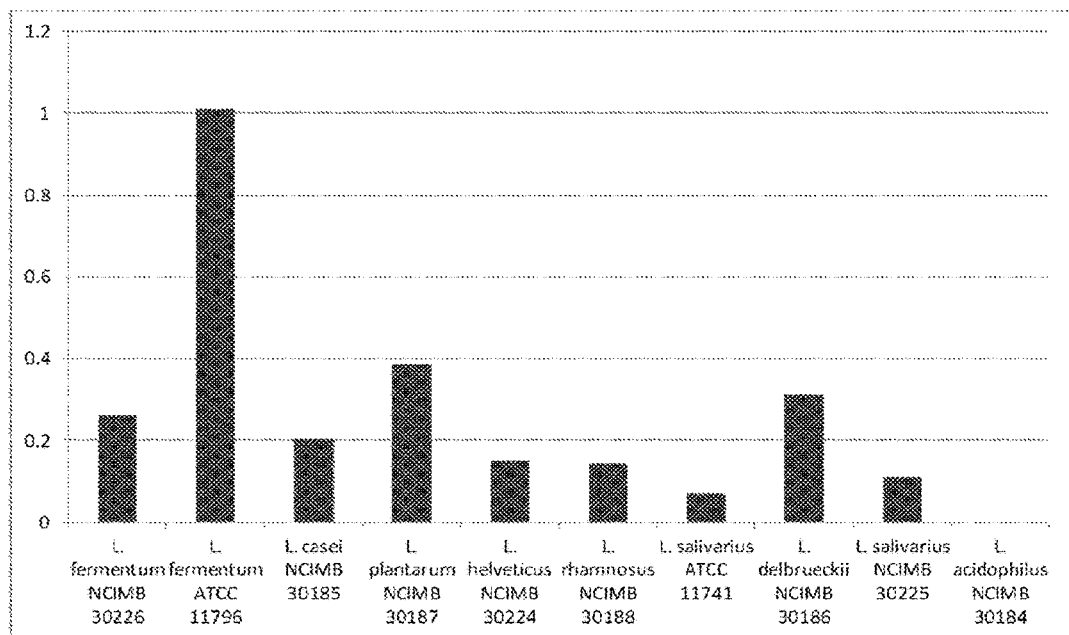
Figure 5C:
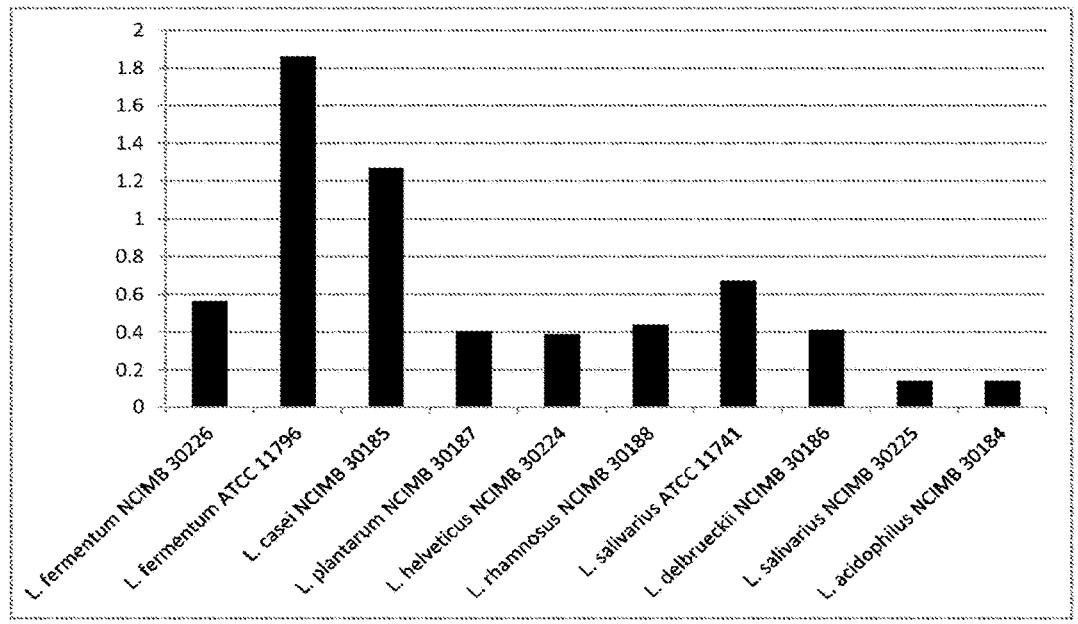
Figure 6A:
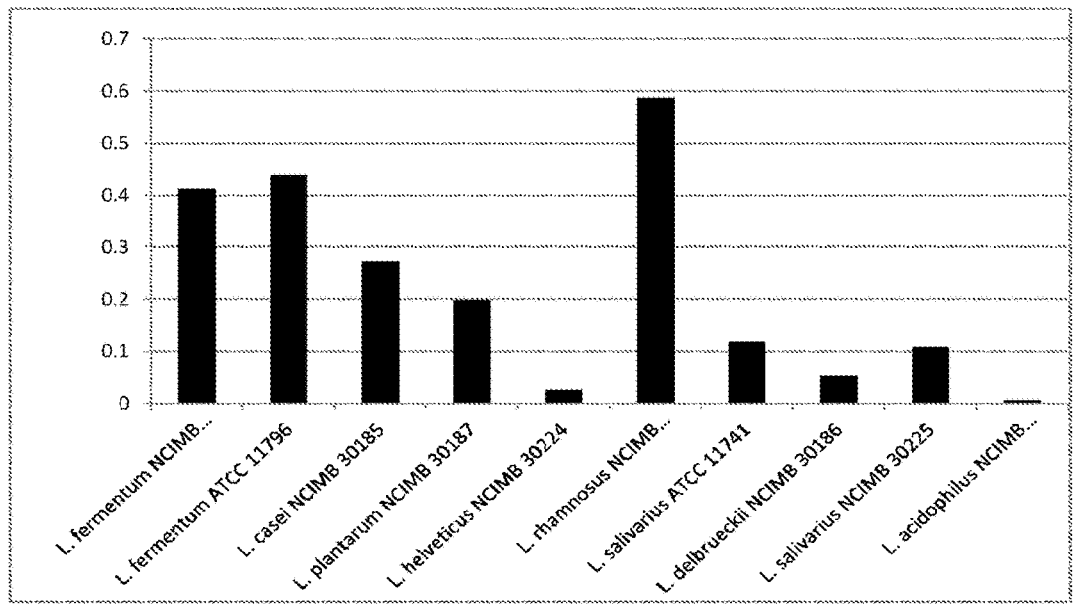
FIG. 6A-6C are graphs show the results of a range of lactobacilli species which were screened for β-galactosidase activity measured at uM of o-NP in A MRS broth, B 1% lactose basal media and C 5% lactose basal media.
Figure 6B:
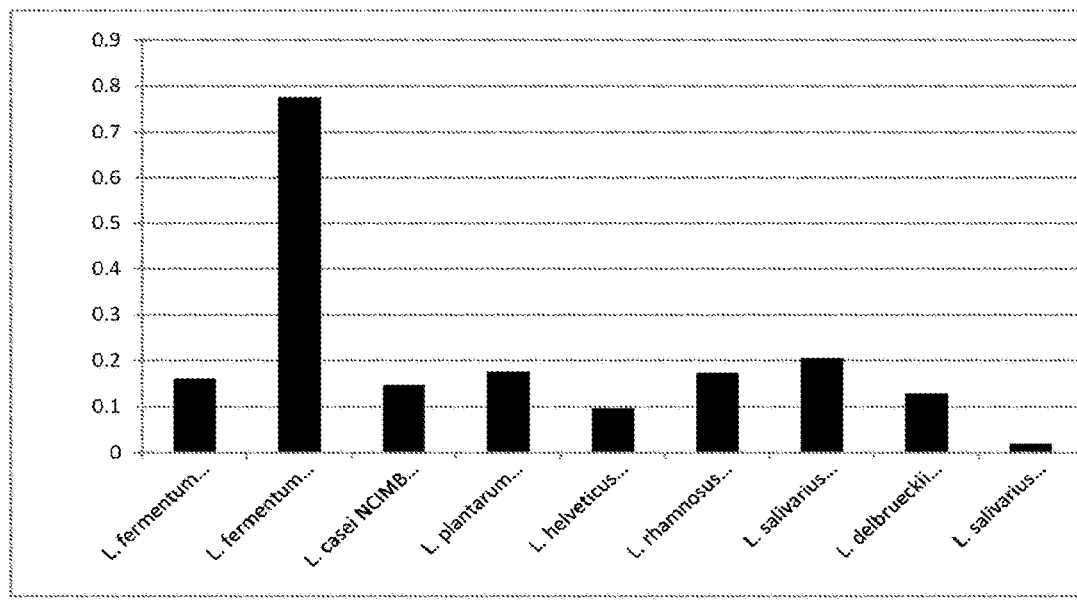
Figure 6C:
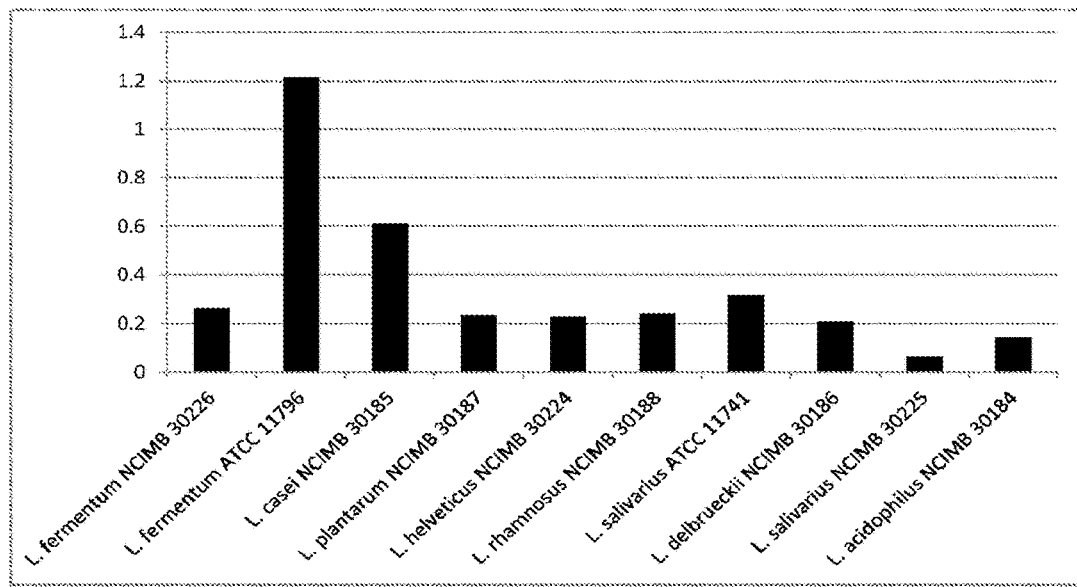

In these experiments, 10 lactobacilli species were screened for β-galactosidase activity in triplicate using standard enzyme assay with o-NPG as substrate. The experiments were carried out in 3 different media; MRS, 1% and 5% lactose in basal media, as lactose is the primary substrate for β-galactosidase it was expected to exhibit highest activity. Activity was measured at time points between time 0-24 hrs, highest activity was shown after 24 hrs. As shown in FIGS. 5-6, in general, 5% lactose exhibits highest enzyme activity and tends to be higher than in MRS broth (contains only glucose as carbon source). High enzyme activity is essential for generating GOS, the 3 organisms which show overall high activity include both *L. fermentum* strains and *L. casei*.

GOS Produced from *L. fermentum* ATCC 11976 and *L. fermentum* NCIMB 30226 in a Long Time Period In these experiments, *L. fermentum* ATCC 11976 and *L. fermentum* NCIMB 30226 were assessed for their production (and consumption) of GOS, lactose and monosaccharides over 168 hours.

Figure 7:
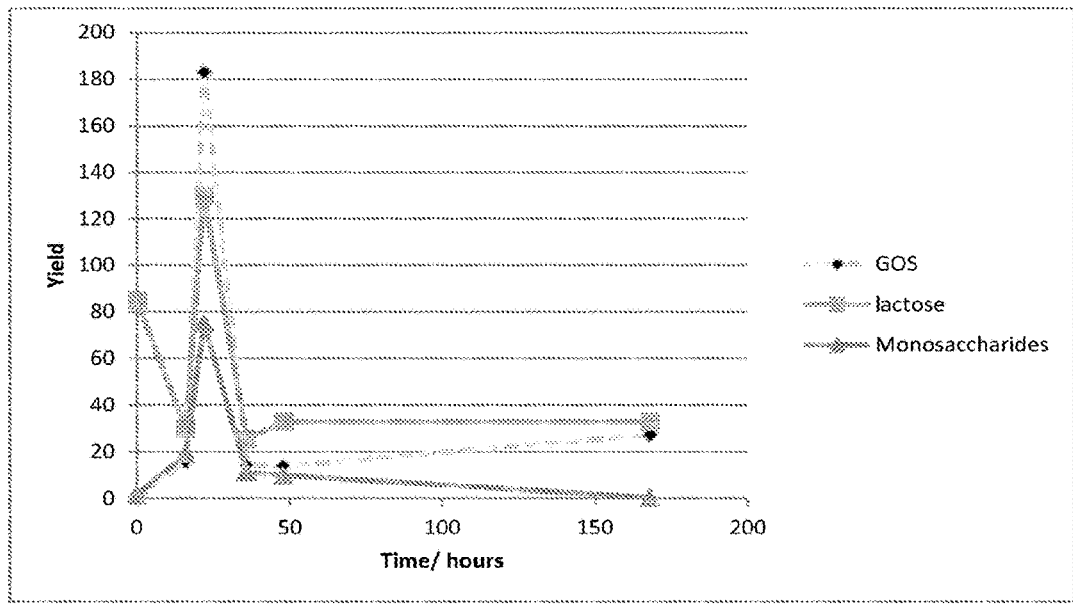
FIG. 7 is a graph showing the yield of GOS, lactose and monosaccharides by *L. fermentum* ATCC 11976 over 168 hours.

The yield of GOS, lactose and monosaccharides for *L. fermentum* ATCC 11976 is shown in the below and in FIG. 7:

| Time point | GOS | lactose | Monosaccharides | Total | GOS %= |
|---|---|---|---|---|---|
| 0 | 0.601 | 85 | 1.464 | 87.065 | 0.690289 |
| 16 | 15.65 | 30.077 | 18.92 | 64.647 | 24.20839 |
| 22 | 183 | 130 | 75 | 388 | 47.16495 |
| 36 | 14.4 | 25.6 | 11.45 | 51.45 | 27.98834 |
| 48 | 14 | 33 | 10 | 57 | 24.5614 |
| 168 | 27.4 | 32.971 | 0.5 | 60.871 | 45.01322 |

Figure 8:
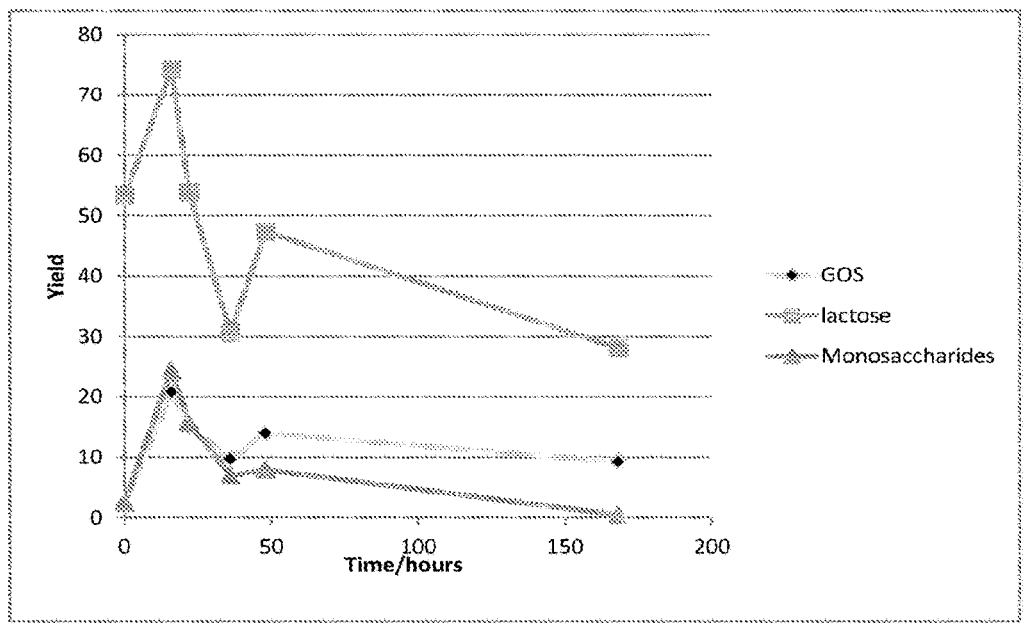
FIG. 8 is a graph showing the yield of GOS, lactose and monosaccharides by *L. fermentum* NCIMB 30226 over 168 hours.

The yield of GOS, lactose and monosaccharides for *L. fermentum* NCIMB 30226 is shown in the below and in FIG. 8:

| Time point | GOS | lactose | Monosaccharides | Total | GOS %= |
|---|---|---|---|---|---|
| 0 | 2.206 | 53.309 | 2.538 | 58.053 | 3.799976 |
| 16 | 20.789 | 74.275 | 24.481 | 119.545 | 17.3901 |
| 22 | 15.066 | 53.918 | 15.713 | 84.697 | 17.78812 |
| 36 | 9.699 | 30.672 | 6.977 | 47.348 | 20.4845 |
| 48 | 13.971 | 47.341 | 7.944 | 69.256 | 20.17298 |
| 168 | 9.3 | 28.125 | 0.521 | 37.946 | 24.50851 |

GOS Produced from *L. fermentum* ATCC 11976 in a 20% Lactose Medium Over 24 Hours In this experiment, GOS synthesis from *L. fermentum* ATCC 11976 β-galactosidase was investigated. After lysis, the crude extract was incubated in 20% lactose over 24 hr and samples taken at time 0 and 24.

The table below shows the sugars present at T0:

| No. | Ret. Time min | Height v | Width min | Type | Asym. (EP) | Plates (EP) | |
|---|---|---|---|---|---|---|---|
| 1 | 0.226 | 0.397 | n.a. | BM | n.a. | n.a. | |
| 2 | 0.689 | 0.283 | n.a. | MB | n.a. | n.a. | |
| 3 | 6.912 | 1.743 | n.a. | Ru | n.a. | n.a. | |
| 4 | 8.436 | 1.465 | n.a. | Ru | n.a. | n.a. | |
| 5 | 9.072 | 1.234 | n.a. | Ru | n.a. | n.a. | |
| 8 | 10.716 | 13.758 | 1.419 | BMb | 0.87 | 851 | |
| 7 | 14.403 | 0.605 | n.a. | Ru | n.a. | n.a. | |
| 8 | 18.457 | 16.603 | n.a. | bM | n.a. | n.a. | |
| 9 | 18.694 | 17.001 | n.a. | M | n.a. | n.a. | |
| 10 | 22.318 | 0.373 | n.a. | Ru | n.a. | n.a. | |
| 11 | 24.168 | 29.345 | 29.609 | M | n.a. | n.a. | |
| 12 | 28.157 | 150.287 | 1.544 | MB | n.a. | 5436 | Lactose |
| n.a. | n.a. | n.a. | n.a. | n.a. | n.a. | n.a. | |
| Average: | | 19.424 | 10.857 | | 0.87 | 3144 | |

The table below shows the sugars present at T24:

| Ret. Time min | Height v | Width min | Type | Resol. (EP) | Asym. (EP) | Plates (EP) | |
|---|---|---|---|---|---|---|---|
| 2.506 | 0.010 | n.a. | BMB | n.a. | 1.52 | 128 | |
| 6.903 | 0.097 | n.a. | BM | n.a. | n.a. | n.a. | |
| 10.624 | 10.367 | 1.121 | M | 1.75 | n.a. | 1425 | |
| 15.062 | 3.082 | 3.812 | MB | 2.17 | n.a. | 232 | |
| 20.868 | 1.220 | 1.268 | BMB | 2.66 | 0.65 | 3522 | |
| 24.177 | 10.614 | 1.097 | BMb | 3.50 | 1.57 | 7869 | GOS |
| 28.167 | 73.205 | 1.207 | bM | n.a. | 1.45 | 8860 | Lactose |
| 29.600 | 5.009 | 2.231 | M | n.a. | n.a. | n.a. | |
| 32.806 | 10.232 | 1.873 | M | 1.05 | n.a. | 5038 | Glucose |

-continued

| Ret. Time min | Height v | Width min | Type | Resol. (EP) | Asym. (EP) | Plates (EP) | |
|---|---|---|---|---|---|---|---|
| 34.822 | 8.609 | 2.038 | M | n.a. | n.a. | 4812 | Galactose |
| 41.161 | 0.867 | n.a. | M | n.a. | n.a. | n.a. | |
| 43.560 | 0.590 | n.a. | M | n.a. | n.a. | n.a. | |
| 46.616 | 0.386 | n.a. | M | n.a. | n.a. | n a | |
| 49.693 | 0.107 | n.a. | MB | n.a. | n.a. | n.a. | |
| 51.010 | 0.006 | n.a. | bMB | n.a. | n.a. | n.a. | |
| 54.025 | 0.006 | n.a. | BMB | 1.18 | 1.41 | 774387 | |
| 54.751 | 0.008 | n.a. | BMB | n.a. | 1.27 | 48500 | |
| n.a. | n.a. | n.a. | n.a. | n.a. | n.a. | n.a. | |
| | 7.319 | 1.831 | | 2.05 | 1.31 | 85477 | |

GOS Produced from *L. fermentum* ATCC 11976 and *L. fermentum* NCNB 30226 in a Short Time Period In this experiment, GOS was produced from *L. fermentum* ATCC 11976 and *L. fermentum* NCIMB 30226 and the enzyme activity of the sugars vs the % GOS assessed over 50 hours as this was when most activity took place during the previous experiments.

Protocol

GOS was produced using the following protocol:
1. Set up 50 ml overnight cultures in modified MRS broth supplemented with 2% lactose for *L. fermentum* ATCC 11976 and *L. fermentum* NCIMB 30226;
2. Suspend 50 ml of overnight culture in 1L of mMRS broth with 2% lactose;
3. Incubate in anaerobic cabinet at 37° C.;
4. *L. fermentum* ATCC 11976 for 14 hours;
5. *L. fermentum* NCIMB 30226 for 8 hours;
6. Measure $OD_{600}$;
7. Centrifuge cultures, 10 000 g×10 mins;
8. Make up 40% lactose in sodium phosphate buffer. 400 g/L;
9. Pour off supernatant;
10. Resuspend pellets in sodium phosphate buffer (50 mM, pH 6.8);
11. Pool pellets in 50 ml falcons;
12. Freeze thaw in Liquid Nitrogen ×3;
13. French Press, 30,000 PSI, 1 pass, 5 drops/min;
14. Spin down lysate-15,000 g×45 min;
15. Pour supernatant into fresh falcon;
16. Carry out β gal activity assay to work enzyme concentrations;
17. Incubate the free cell extract with 40% lactose/sodium phosphate buffer;
18. Sample 200 μl every 2 hours over 50 hours;
19. Freeze samples;
20. Filter sterilise all samples through 0.2 μm filter;
21. Analyse on HPLC.

Results—GOS Production

As shown in FIGS. 9 to 12, there was a 30-45% lactose conversion and 10% GOS yield.

Enzyme Activity

A further experiment was conducted in order to ascertain the enzyme activity (and therefore efficiency) of the GOS produced from *L. fermentum* ATCC 11976 and *L. fermentum* NCIMB 30226.

Cultures were grown for 8 hrs F, 14 hr for F* in 1L and harvested at 12,000 g×10 min. The cells were lysed and cell extract spun down 15.000 g×45 min. This was then incubated at 40° C. in 40% lactose sodium phosphate buffer +MgCl$_2$ with same U of enzyme/reaction and activity analysed on an HPLC at 2 hour time points for 36 hours.

The enzyme unit calculations were as follows:

| Organism | OD pre harvest | $OD_{420}$ (enzyme) after french press | $OD_{420}$ (enzyme) after final spin | Enzyme U/15 ml |
|---|---|---|---|---|
| F*1 | 0.83 | 2.4605 | 2.3315 | 18.23977 |
| F*2 | 0.86 | 1.83 | 3.1955 | 30.17002 |
| F1 | 0.94 | 1.833 | 3.812 | 30.0665 |
| F2 | 1.13 | 1.5739 | 6.0115 | 47.63684 |

Where F*1, F2 18U/reaction, F*2, F1 30 U/reaction.

Results

As shown in FIGS. 13 to 16, there was a 40-50% lactose conversion and 15-20% GOS yield.

Lactobacilli Specificity with GOS Purity

In this experiment, GOS produced from *L. fermentum* ATCC 11976 used as part of the growth media for a range of bacteria to see if this species specific GOS provided any growth specificity.

GOS Synthesis

*L. fermentum* ATCC 11976 was grown in modified MRS supplemented with 2% lactose in 1L cultures for 14 hours. The culture was spun down and re-suspend in a sodium phosphate buffer. The cells were lysed using liquid Nitrogen and a French Press and the lysate spun to obtain free cell extract. The free cell extract was incubated with 40% Lactose and a sample taken every 2 hours over 50 hours. Samples were loaded on HPLC after every time point for analysis, Growth Curves 20% GOS Mixture 1% of the impure GOS produced earlier was added to 9 ml mMRS hungates. The growth of a range of organisms were on this mixture were analysed: *Clostridium difficile, Bifidobacterium bifidum, Bifidobacterium longum, Lactobacillus fermentum* ATCC 11976, *Lactobacillus fermentum, Lactobacillus rhamnosus, Lactobacillus casei & Lactobacillus delbrueccki*. Experiments were conducted in 3 repeats in triplicate with enumeration at 0, 3, 6, 8, 16 and 24 hours.

Results

Figure 17:
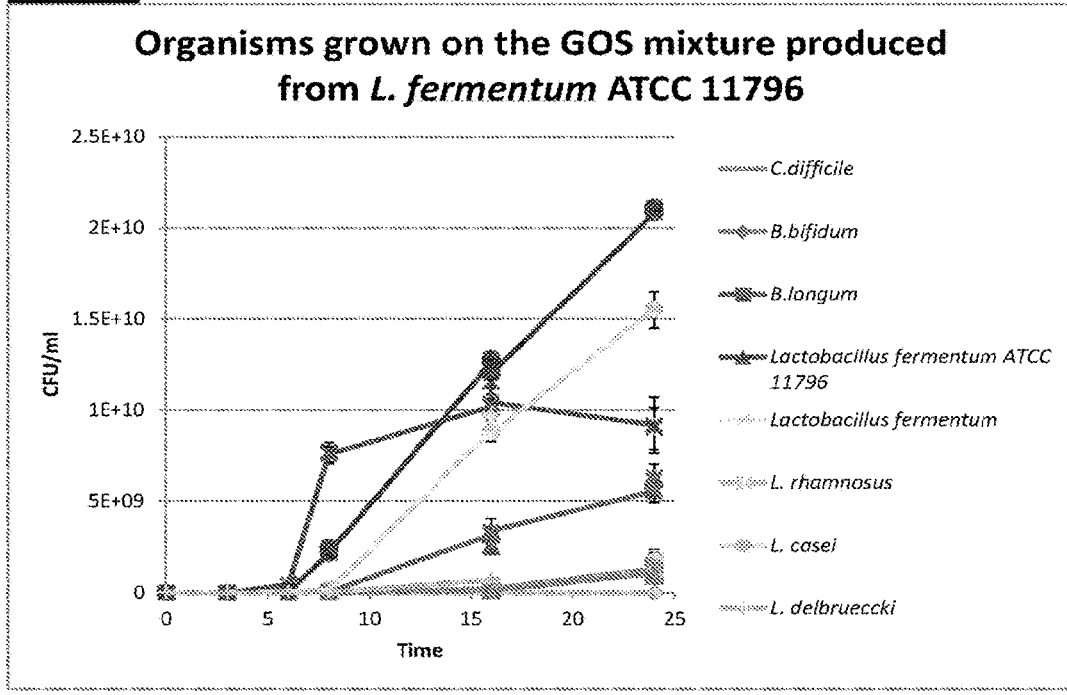
FIG. 17 is a graph illustrating the relative growth profiles of a range of bacteria grown on a GOS mixture produced from *L. fermentum* ATCC 11976.
Figure 18:
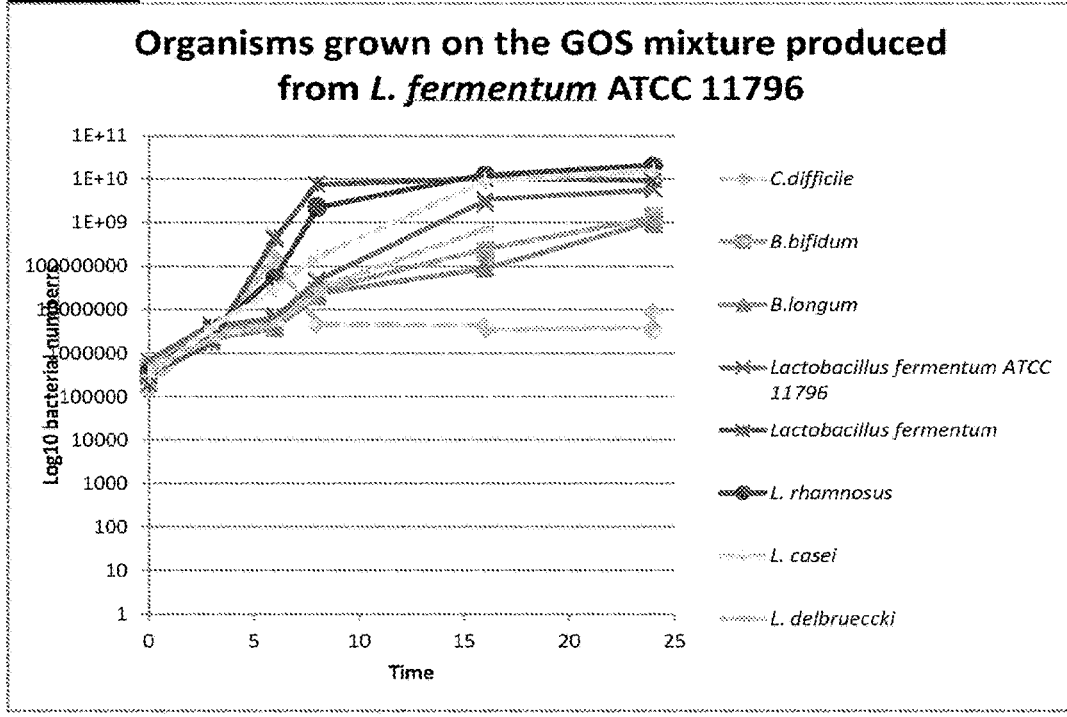
FIG. 18 is a second graph illustrating the relative growth profiles of a smaller range of bacteria grown on a GOS mixture produced from *L. fermentum* ATCC 11976.

As shown in FIGS. 17 and 18, little growth was found in *C. difficile*, whereas the best growth was found in *L. rhamnosus*. The 20% GOS mixture as generally more selective towards lactobacilli.

The forgoing embodiments are not intended to limit the scope of the protection afforded by the claims, but rather to describe examples of how the invention may be put into practice.

The invention claimed is:

1. A prebiotic composition comprising a microbially produced oligosaccharide, wherein the oligosaccharide is characterised by being selective for a pre-determined probiotic bacterial strain and also capable of being produced by the pre-determined probiotic bacterial strain by reverse enzyme reaction;

wherein the pre-determined probiotic bacterial strain is a *Lactobacilli* strain selected from a group consisting of *Lactobacillus acidophilus, Lactobacillus rhamnosus, Lactobacillus plantarum, Lactobacillus delbrueckii* ssp. *bulgaricus, Lactobacillus casei, Lactobacillus salivarius, Lactobacillus salivarius* ssp. *salivarius, Lactobacillus fermentum, Lactobacillus helveticus*, and combinations thereof;

wherein the enzyme is a β-galactosidase; and wherein the oligosaccharide comprises galacto oligosaccharide (GOS), the GOS is substantially the same as the form produced by reverse β-galactosidase reaction in the probiotic bacterial strain, and the GOS comprises β1-4 linkages.

2. A composition as claimed in claim 1, wherein the composition is encapsulated.

3. A composition as claimed in claim 1, wherein the composition further comprises an excipient or carrier compound to enable it to pass through the gastrointestinal environment of the body and retain its functional properties.

4. A composition as claimed in claim 1, wherein the composition is in the form of a drinkable liquid and/or can be mixed with a solid or liquid food stuff.

5. A composition as claimed in claim 1 wherein the composition is a medicament.

6. A composition as claimed in claim 1 wherein the composition is a dietary supplement.

7. A composition as claimed in claim 1 wherein the composition is a cholesterol lowering agent.

8. A composition as claimed in claim 1 wherein the composition is an anti-metabolic syndrome agent.

9. A composition as claimed in claim 1 wherein the composition is a weight management agent.

10. A composition as claimed in claim 1 wherein the composition is an anti-diabetic agent.

11. A method of screening a composition of claim 1 which is suitable for use as a prebiotic comprising the steps: (a) assembling a panel of probiotic bacterial strains; (b) selecting a strain found to have oligosaccharide activity; (c) inducing the selected probiotic strain to produce an oligosaccharide prebiotic composition by reverse enzyme reaction; and (d) isolating the oligosaccharide prebiotic composition; wherein the probiotic bacterial strain is a *Laciobacillus plantarum* strain selected from a group consisting of *Lactobacillus acidophilus, Lactobacillus rhamnosus, Lactobacillus plantarum, Lactobacillus delbrueckii* ssp. *bulgaricus Lactobacillus casei, Lactobacillus salivarius Lactobacillus salivarius* ssp. *salivarius, Lactobacillus fermentun, Lactobacillus helveticus*, and combinations thereof; and wherein the oligosaccharide comprises galacto oligosaccharide (GOS) and the GOS is substantially the same as the form produced by reverse P-galactosidase reaction in the probiotic bacterial strain.

12. A method as claimed in claim 11, wherein the method further comprises:
(f) assessing growth and/or survivability of the selected probiotic bacterial strain using the isolated oligosaccharide prebiotic composition.

13. A method as claimed in claim 11 or use in producing a prebiotic composition as claimed in claim 1.

* * * * *